United States Patent [19]

Peglion et al.

[11] Patent Number: 5,134,147
[45] Date of Patent: Jul. 28, 1992

[54] 1,2-BENZISOXAZOLE COMPOUNDS

[75] Inventors: Jean L. Peglion; Francis Colpaert, both of le Vesinet, France

[73] Assignee: Adir et Compagnie, Courbevoie, France

[21] Appl. No.: 779,828

[22] Filed: Oct. 21, 1991

Related U.S. Application Data

[62] Division of Ser. No. 604,789, Oct. 26, 1990.

[30] Foreign Application Priority Data

Nov. 7, 1989 [FR] France .................. 89 14571

[51] Int. Cl.$^5$ .................. A61K 31/445; C07D 521/00
[52] U.S. Cl. .................... 514/300; 546/172; 546/198; 546/326; 546/333; 546/334; 546/339; 546/341; 546/342; 546/343; 548/241; 548/531; 548/572
[58] Field of Search ............ 546/122; 514/300

[56] References Cited

U.S. PATENT DOCUMENTS 4,472,193 9/1984 Turner .................. 546/122
4,528,376 7/1985 Strupczewski et al. ......... 546/198

FOREIGN PATENT DOCUMENTS

WO91/08208 6/1991 PCT Int'l Appl. .................. 546/122

Primary Examiner—C. Warren Ivy
Assistant Examiner—James H. Turnipseed
Attorney, Agent, or Firm—Gordon W. Hueschen

[57] ABSTRACT

Compounds of formula I

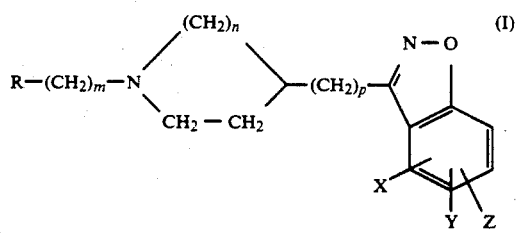

in which
m represents an integer from 0 to 5, n represents an integer from 1 to 2, p is equal to 0, 1 or 2,
X, Y and Z, which may be identical or different, each represent a hydrogen atom, a halogen atom, a linear or branched alkyl radical, a trifluoromethyl radical, an alkoxy radical, an alkylthio radical or a hydroxyl radical, and
R represents a 2-benzofuranyl or 2,3-dihydro-2-benzofuranyl radical (it being possible for each to be substituted on the benzene ring), a 2,3,6,7-tetrahydrobenzo[1,2-b:4,5-b']difuran-2-yl radical, a 4-oxo-4H-chromen-2-yl radical (optionally substituted on the benzene ring), a benzocyclobutenyl radical of formula A or an indanyl radical of formula B:

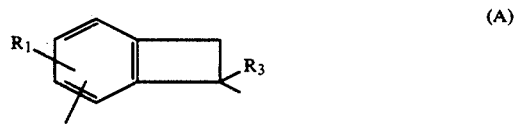

(A)

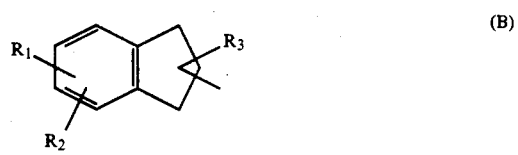

(B)

(in which: $R_1$ and $R_2$, which may be identical or different, each represent a hydrogen atom, a halogen atom, a trifluoromethyl radical, an alkyl radical, an alkoxy radical, a hydroxyl radical, a hydroxyalkyl radical or an alkylthio radical, or together form a methylenedioxy radical or an ethylenedioxy radical, and $R_3$ represents a hydrogen atom or a linear or branched alkyl radical having 1 to 6 carbon atoms), or a radical of formula C:

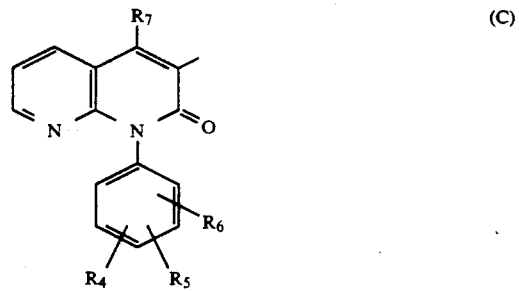

(C)

(in which $R_4$, $R_5$ and $R_6$, which may be identical or different, each represent a hydrogen atom, a halogen atom, a trifluoromethyl radical, a hydroxyl radical, an alkyl radical, an alkoxy radical or an alkylthio radical, their optical isomers and their addition salts with a pharmaceutically acceptable organic or inorganic acid.

6 Claims, No Drawings

1,2-BENZISOXAZOLE COMPOUNDS

This application is a division of our prior-filed co-pending application Ser. No. 07/604,789, filed Oct. 26, 1990.

The present invention relates to new 1,2-benzisoxazole compounds, to processes for preparing these and to pharmaceutical compositions containing them.

A large number of 3-piperidyl-1,2-benzisoxazole compounds are known in the literature. Applications EP 196,132 and EP 314,098 as well as U.S. Pat. No. 4,352,811 describe derivatives substituted at the 1-position of the piperidine ring with heterocycles containing 2 or 3 hetero atoms or with compounds of the phenyl ring. These compounds are endowed with antipsychotic properties. 3-Piperidyl-1,2-benzisoxazole compounds having analgesic or neuroleptic properties are also known (U.S. Pat. No. 4,469,869 and U.S. Pat. No. 4,355,037; Patent Application EP 080,104; J. Med. Chem (1985) 28 p. 761-769).

The compounds of the present invention are 3-piperidyl- and 3-pyrrolidinyl-1,2-benzisoxazole derivatives, and are distinguished from the already known compounds by their substituents at the 1-position of the piperidine and pyrrolidine ring and by their pharmacological properties. In effect, various pharmacological tests have demonstrated that the compounds of the invention are dopamine and serotonin antagonists, and possess an antipsychotic activity comparable to that of haloperidol, a reference substance for the evaluation of antipsychotics, but, at the active doses, do not induce side effects, and in particular extrapyramidal effects. In point of fact, it is known that antipsychotics can produce very considerable side effects, and this factor can limit their use. The compounds of the invention hence constitute a new class of antipsychotics and find their application as sedatives, anxiolytics, aggression inhibitors and analgesics. They are also useful for the treatment of schizophrenia and that of depression.

The subject of the present invention is, more especially, 1,2 benzisoxazole compounds of the general formula I:

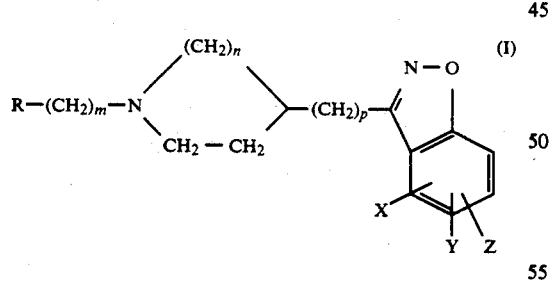

in which
m is selected from the group consisting of : zero and the integers from 1 to 5,
n is selected from the group consisting of : integers from 1 to 2,
p is selected from the group consisting of : 0, 1 and 2,
X, Y and Z, which may be identical or different, are each selected from the group consisting of a hydrogen atom, halogen atoms, linear and branched alkyl radicals having 1 to 6 carbon atoms, a trifluoromethyl radical, alkoxy radicals having 1 to 6 carbon atoms, alkylthio radicals having 1 to 6 carbon atoms and a hydroxyl radical, and R is selected from the group consisting of 2-benzofuranyl and 2,3-dihydro-2-benzofuranyl radicals (and each of them substituted on the benzene ring with one and more halogen atoms, with alkoxy radicals having 1 to 6 carbon atoms, with alkylthio radicals having 1 to 6 carbon atoms and with linear and branched alkyl radicals having 1 to 6 carbon atoms), a 2,3,6,7-tetrahydrobenzo[1,2-b:4,5-b'] difuran-2-yl radical, a 4-oxo-4H-chromen-2-yl radical (and this latter 5 substituted on the benzene ring with one and more halogen atoms, with linear and branched alkyl radicals having 1 to 6 carbon atoms and with alkoxy radicals having 1 to 6 carbon atoms), a benzocyclobutenyl radical of formula A and an indanyl radical of formula B:

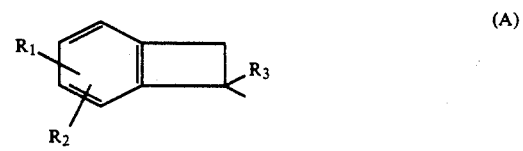

(A)

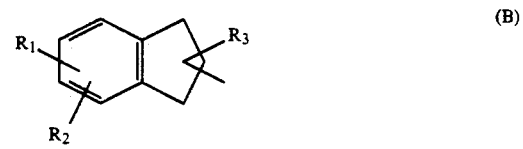

(B)

in which
$R_1$ and $R_2$, which may be identical or different, are each selected from the group consisting of a hydrogen atom, halogen atoms, a trifluoromethyl radical, linear and branched alkyl radicals having 1 to 6 carbon atoms, alkoxy radicals having 1 to 6 carbon atoms, a hydroxyl radical, hydroxyalkyl radicals having 1 to 6 carbon atoms, and alkylthio radicals having 1 to 6 carbon atoms, and together form a methylenedioxy radical and an ethylenedioxy radical,
and $R_3$ is selected from the group consisting of a hydrogen atom, linear and branched alkyl radicals having 1 to 6 carbon atoms, and a radical of formula C:

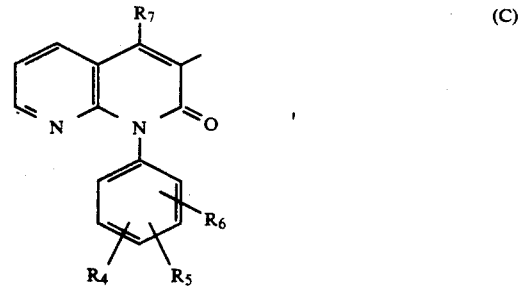

(C)

in which
$R_4$, $R_5$ and $R_6$, which may be identical or different, are each selected from the group consisting of a hydrogen, atom, a halogen atom, a trifluoromethyl radical, a hydroxyl radical, linear and branched alkyl radicals having 1 to 6 carbon atoms, alkoxy radicals having 1 to 6 carbon atoms, and alkylthio radicals having 1 to 6 carbon atoms,
and $R_7$ is selected from the group consisting of a hydrogen atom and a hydroxyl radical, their optical isomers and their addition salts with a pharmaceutically acceptable organic or inorganic acid.

The subject of the present invention is also a process for preparing the compounds of general formula I, wherein:
either
a compound of formula II:

in which R and m have the same meaning as for the formula I and W represents a halogen atom, a tosyloxy radical or a mesyloxy radical, is reacted
either
with a compound of formula III:

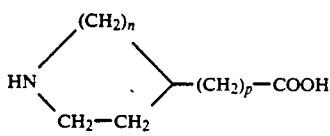

in which n and p have the same meaning as for the formula I, in the presence of N,N-diethylethylenediamine in dimethylformamide or in another equivalent organic solvent,
to form a compound of formula IV:

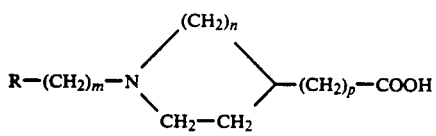

in which R, m, n and p have the meaning stated above for the formula I,
which is subjected to the action of thionyl chloride or oxalyl chloride to form an acid chloride of formula V:

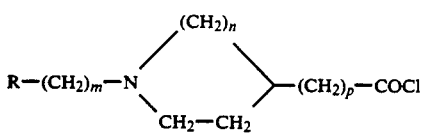

in which the meaning of R, m, n and p remains identical to that given above for the formula I,
which is condensed in the presence of aluminum chloride with a compound of formula VI:

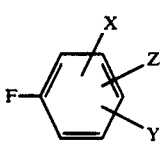

in which X, Y and Z have the same meaning as for the formula I,
to form a compound of formula VII:

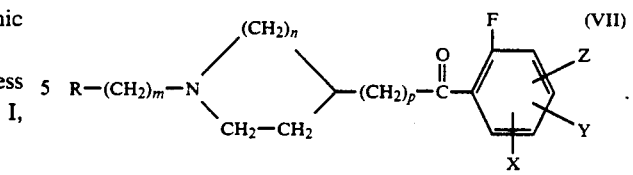

in which R, X, Y, Z, m, n and p have the same meaning as for the formula I,
which is subjected to the action of hydroxylamine hydrochloride in the presence of 2-(diethylamino)ethylamine in an alcoholic medium,
to obtain a compound of formula VIII:

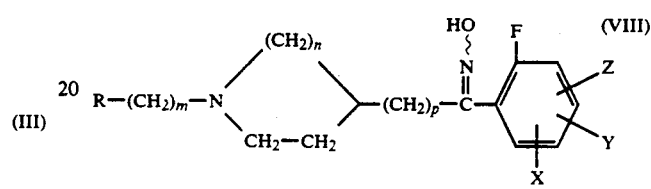

in which the meaning of R, X, Y, Z, m, n and p remains identical to that given above for the formula I,
which is cyclized by means of a strong inorganic base to obtain the compounds of the formula I,
or
with a compound of formula IX:

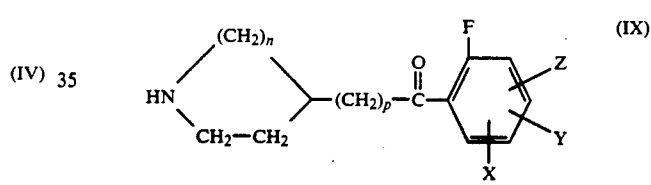

in which X, Y, Z, n and p have the same meaning as for the formula I, in the presence of N,N-diethylethylenediamine in dimethylformamide or another equivalent organic solvent,
to form the compounds of formula VII, from which are obtained the compounds of formula VIII and then the compounds of formula I according to the process described above,
or
with a compound of formula X:

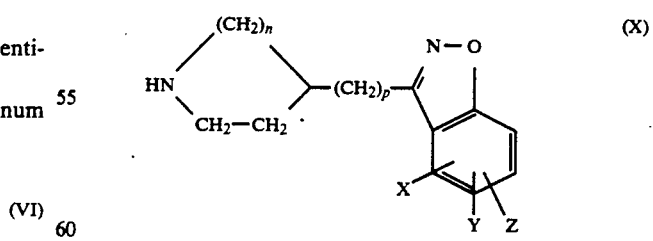

in which X, Y, Z, n and p have the same meaning as for the formula I, in the presence of N,N-diethylethylenediamine in dimethylformamide or another equivalent organic solvent,
to form the compounds of formula I,
or
a compound of formula $XI_A$ or $XI_B$:

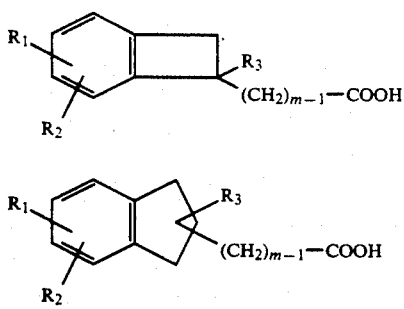

(XI_A)

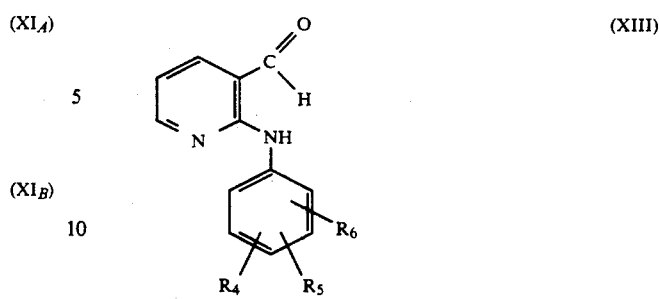

(XIII)

in which $R_1$, $R_2$, $R_3$ and m have the same meaning as for the formula I except that, in this case, m cannot represent the number 0,
is reacted with a compound of formula X, in the presence of carbonyldiimidazole, to form a compound of formula $XII_A$ or $XII_B$:

In which $R_4$, $R_5$ and $R_6$ have the same meaning as for the formula I, is reacted with a compound of formula XIV:

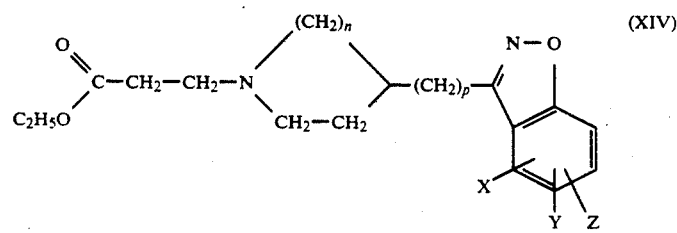

in which the meaning of n, p, X, Y and Z remains identical to that given for the formula I, to form the compounds of formula I in which R represents a radical of formula C and m is equal to 1,

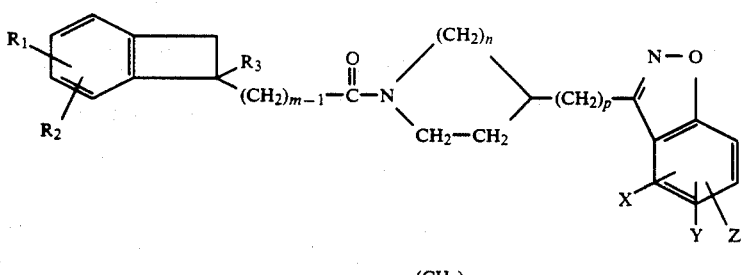

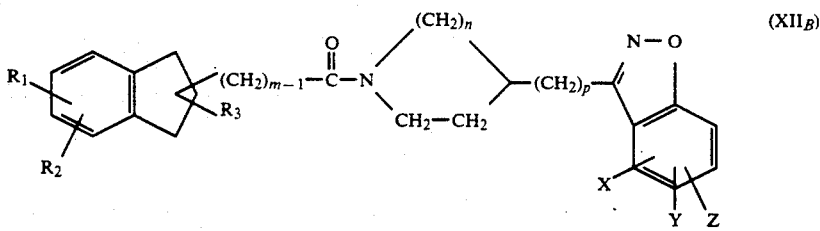

in which $R_1$, $R_2$, $R_3$, m, n, p, X, Y and Z have the meaning given for the formula I except that, in this case, m cannot represent the number 0,
which is subjected to the action of lithium aluminum hydride,
to form the compounds of formula I,
or
a compound of formula XIII:

which compounds of formula I
may be salified with a pharmaceutically acceptable inorganic or organic acid to form the corresponding salts, or
be separated into their optical isomers and then salified.

The compounds of formula II, when R represents a 4-oxo-4H-chromen-2-yl radical, are prepared from 2-hydroxyacetophenone and ethyl 2-methylthioacetate (J. Org. Chem., (1984), 49, p. 5038).

When R represents a 2-benzofuranyl or 2,3-dihydro-2-benzofuranyl radical, the compounds of formula II are prepared, respectively, from ethyl 2-benzofurancarboxylate (J.A.C.S., (1951), 73, p. 872) or 2,3-dihydro-2-benzofurancarboxylic acid (Chim. Ter., (1973), 3, p. 259). These two compounds are subjected to the action of lithium aluminum hydride to obtain the corresponding alcohols, which enable the compounds of formula II to be obtained by conventional methods.

The compounds of formula II, when R represents a radical (A), are obtained from the acids of formula XI$_A$ according to a process already described in the literature (J.A.C.S., (1975), 154, p. 347). The processes for the synthesis of the acids of formula IX$_A$ or their derivatives are also known (J.A.C.S., (1958), 80, p. 2257; J.A.C.S., (1975), 154, p. 347; J. Org. Chem., (1972), 32, p. 820; J. Org. Chem., (1968), 33, p. 3327; Tet. Lett., (1973), 29, p. 73).

The compounds of formula IX, when n is equal to 2, may be prepared from the compounds of formula III$_A$:

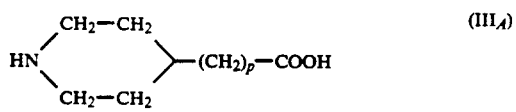
(III$_A$)

in which p has the same meaning as for the formula I.

The compounds of formula III$_A$ are subjected to the action of acetic anhydride to form the compounds of formula XV:

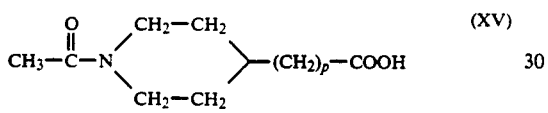
(XV)

in which the meaning of p remains identical to that given for the formula I.

The corresponding acyl halides are then obtained by conventional methods, and condensed with a compound of formula VI to obtain a compound of formula XVI:

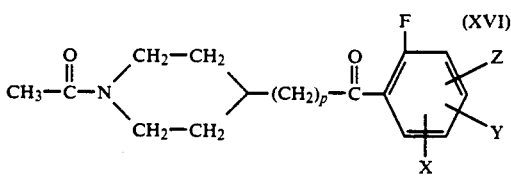
(XVI)

in which X, Y, Z and p have the same meaning as for the formula I. From these compounds, with conventional methods (deprotection of the amine), the expected compounds are obtained.

To obtain the compounds of formula X (n=2), the compounds of formula IX (n=2), mentioned above, are subjected to the action of hydroxylamine hydrochloride in the presence of N,N-diethylethylenediamine to obtain the compounds of formula XIV:

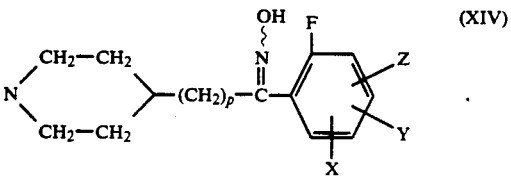
(XIV)

in which the meaning of p, X, Y and Z remains identical to that given for the formula I. These compounds enable the expected compounds to be obtained by conventional methods already mentioned.

The compounds of formula X, when n is equal to 1, are obtained from benzylamine and itaconic acid, which are condensed in the heated state to obtain 1-benzyl-2-oxo-4-pyrrolidinecarboxylic acid. This acid is subjected to the action of lithium aluminum hydride to obtain 1-benzyl-3-(hydroxymethyl)pyrrolidine, which is converted by means of thionyl chloride to 1-benzyl-3-(chloromethyl)pyrrolidine and then to 1-benzyl-3-(cyanomethyl)pyrrolidine by conventional methods. The latter compound is then hydrolyzed with strong inorganic bases to 2-(1-benzyl-3-pyrrolidinyl)acetic acid, which is either, after conversion to the acid chloride, reacted in the presence of aluminum chloride with a compound of formula VI to obtain a compound of formula XVII$_A$:

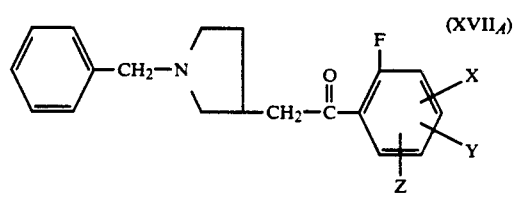
(XVII$_A$)

In which X, Y and Z have the same meaning as for the formula I, or first converted by known processes to 3-(1-benzyl-3-pyrrolidinyl)propionic acid and then to the acid chloride, and thereafter reacted with a compound of formula VI to obtain a compound of formula XVII$_B$:

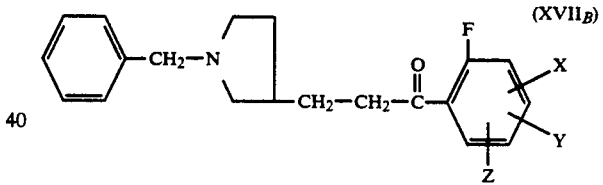
(XVII$_B$)

The compounds XVII$_A$ and XVII$_B$ are subjected to the action of hydroxylamine hydrochloride and converted to 1,2-benzisoxazole derivatives by means of a strong base, and then, after deprotection of the nitrogen of the pyrrolidine ring, the expected compounds are obtained.

The optical isomers of the compounds of the formula I, which also form the subject of the present invention, may be obtained by conventional methods (salification with an optically active acid such as, for example, (+)- or (−)-camphorsulfonic acid).

Among pharmaceutically acceptable acids for the preparation of the addition salts with the compounds of general formula I, phosphoric, hydrochloric, citric, hydriodic, oxalic, maleic, sulfuric, tartaric, mandelic, fumaric and methanesulfonic acids, and the like, may be mentioned.

The compounds of the invention, as well as their addition salts, are endowed with highly advantageous pharmacological properties, and are distinguished from other, already known 1,2-benzisoxazole derivatives.

Pharmacological tests have demonstrated their dopamine and serotonin antagonist activity. For example, their capacity to inhibit completely methylphenidate-induced stereotypy in rats may be mentioned. The active doses are approximately 160-fold lower than the dose which causes catalepsy. In effect, it is known that conventional dopamine antagonist neuroleptics—of which the reference compound is haloperidol—block stereotypy induced in rats by dopaminergic agents such as apomorphine, amphetamine or methylphenidate (Janssen P. A. J., Niemegeers J. E. and Schellekens K. H. L. Arzneim. Forsch, (1965), 15, p. 104). For the study of the products of the invention, methylphenidate was used as a dopaminergic agent because it enables an especially representative model of human psychosis to be obtained.

During the pharmacological study, it was found that haloperidol totally inhibits methylphenidate-induced stereotypy at a dose identical to that which causes catalepsy. In point of fact, it is known that the induction of catalepsy is the best factor for evaluation of the side effects of neuroleptics, and in particular the extrapyramidal effects. It is also known that these effects are a factor which limits their use in therapy. The compounds of the invention totally inhibit methylphenidate-induced stereotypy at doses which are very much lower than the cataleptic dose In effect, at active doses, they do not cause catalepsy, and hence constitute a new class of neuroleptics of major importance for therapy.

The compounds of the invention hence find their application in the treatment of diseases necessitating sedatives, anxiolytics, aggression inhibitors and analgesics, or in the treatment of schizophrenia and depression.

The invention also encompasses pharmaceutical compositions containing as active principle at least one compound of general formula I, or one of its addition salts with a pharmaceutically compatible inorganic or organic acid, in combination with one or more suitable inert excipients.

The pharmaceutical compositions thereby obtained are advantageously presented in various forms such as, for example, tablets, dragees, hard gelatin capsules, sublingual tablets or other pharmaceutical dosage forms suitable for sublingual administration, suppositories and solutions for injection or to be taken by mouth.

The dosage can vary widely in accordance with the patient's age and weight, the nature and severity of the condition and also the administration route.

The preferred administration route is the oral or parenteral route. Generally speaking, single doses will range between 0.2 and 100 mg, and the daily dosage usable in human therapy between 0.5 and 500 mg.

The examples which follow, given without implied limitation, illustrate the invention.

The melting points stated are measured according to the micro-Kofler technique. The proton nuclear magnetic resonance (NMR) spectra were recorded at 200 MHz. The spectral physical constants of the compounds of general formula I are shown in Table I.

EXAMPLE 1

(RS)-3-[1-(benzocyclobuten-1-ylmethyl)-4-piperidyl]-6-fluoro-1,2-benzisoxazole hydriodide Process No. 1

Stage A

1-Acetyl-4-piceridinecarboxylic acid 100 g of 4-piperidinecarboxylic acid and 400 ml of acetic anhydride are mixed. The mixture is brought to reflux for 2 hours and then left overnight at room temperature. The reaction medium is concentrated and the residue is ground with ethyl ether, filtered off and then washed with ethyl ether to obtain the expected compound.

Yield: 79%
Melting point: 175° C.

Stage B

1-Acetyl-4-piperidinecarbonyl chloride 52 g of the acid obtained in the preceding stage are added portionwise to 320 ml of thionyl chloride. After stirring overnight, the precipitate formed is filtered off and washed several times with isopropyl ether to isolate the expected product, which is used immediately without further purification.

Yield: 80%

Stage C

1-Acetyl-4-(2,4-difluorobenzoyl)piperidine 54.3 g of aluminum chloride and 130 ml of dichloroethane are mixed. 24 g of 1,3-difluorobenzene are added and the acid chloride obtained in the preceding stage is then added portionwise. The reaction medium is brought to reflux for 6 hours and then left overnight at room temperature. It is hydrolyzed with ice and 190 ml of concentrated hydrochloric acid. The mixture is extracted 5 times with 100 ml of dichloromethane and the organic phase is dried over anhydrous magnesium sulfate to obtain the expected compound.

Yield: 53%
Melting point: 97° C.

Stage D 4-(2,4-Difluorobenzoyl)piperidine 30 g of 1-acetyl-4-(2,4-difluorobenzoyl)piperidine are brought to reflux in 113 ml of 6N hydrochloric acid for 6 hours. The reaction medium is then concentrated and the residue obtained is crystallized in isopropanol. The expected compound is isolated after filtration.

Yield: 83%
Melting point: 230° C.

Stage E 4-(2,4-Difluorobenzoyl)piperidine oxime hydrochloride 3 g of the compound obtained in the preceding stage, 3 g of hydroxylamine hydrochloride and 2.7 g of N,N-diethylethylenediamine are added to 30 ml of ethanol, and the mixture is brought to reflux for 8 hours. It is left overnight at room temperature and filtered and the residue isolated is rinsed with ethanol to obtain 4-(2,4-difluorobenzoyl)piperidine oxime hydrochloride.

Yield: 50%
Melting point: >260° C.

Proton nuclear magnetic resonance spectrum (solvent DMSO-d$_6$):

1.7 ppm, m, 2H; 1.9 ppm, m, 2H; 2.70 ppm, m, 1H; 2.9 ppm, m, 2H; 3.25 ppm, m, 2H; 7.15 ppm, td, 1H; 7.3 ppm, m, 2H; 9.0 ppm, 1H exchangeable; 11.1 ppm, 1H exchangeable.

Stage F

6-Fluoro-3-piperid-4-yl-1,2-benzisoxazole 1 g of the compound obtained in stage E is mixed with 2.3 g of potassium hydroxide and 5 ml of water. The reaction medium is heated to reflux for 4 hours. 20 ml of water are then added and the mixture is extracted 4 times with 50 ml of toluene. The organic phase is dried to obtain, after evaporation of the solvent, 6-fluoro-3-piperid-4-yl-1,2-benzisoxazole.

Yield: 80%

Melting point: 90° C.

Proton nuclear magnetic resonance spectrum (solvent DMSO-$d_6$):

1.75 ppm, gd, 2H; 1.95 ppm, m, 2H; 2.7 ppm, m, 2H; 3.05 ppm, m, 2H; 3.25 ppm, t, 1H; 3.3 ppm, 1H exchangeable; 7.3 ppm, td, 1H; 7.7 ppm, dd, 1H; 8 ppm, dd, 1H

Stage G 1-(Iodomethyl)benzocyclobutene 6 g of benzocyclobuten-1-ylmethyl para-toluenesulfonate (prepared according to the process described in J.A.C.S., (1975), 154, p. 347) are mixed with 6.2 g of sodium iodide in 85 ml of acetone. The reaction medium is brought to reflux for 8 hours, then introduced into 150 ml of water and extracted several times with ethyl ether. The organic phase is then washed with normal sodium thiosulfate solution, dried over anhydrous magnesium sulfate and concentrated to obtain the expected compound in the form of an oil.

Yield: 88%

Proton nuclear magnetic resonance spectrum (solvent CDCl$_3$):

2.85 ppm, d, 1H; 3.3 to 3.6 ppm, m, 3H; 3.9 ppm, m, 1H; 7 to 7.3 ppm, m, 4H.

Stage H 5.54 g of the compound obtained in the preceding stage, 5 g of the compound obtained in stage F and 3.18 ml of triethylamine are mixed in 100 ml of dimethylformamide and then brought to 60° C. for 8 hours. The mixture is then concentrated and the residue is taken up with water. The precipitate formed is filtered off and washed several times with water and then with ethyl ether. It is dried and the compound obtained is recrystallized in methanol.

Yield: 29%

Melting point: 270°–273° C.

| | Elemental analysis: | | | |
|---|---|---|---|---|
| | C % | H % | N % | I % |
| Theory | 54.32 | 4.78 | 6.03 | 27.33 |
| Found | 53.91 | 4.92 | 6.10 | 27.26 |

Process No. 2

Stage A 1-(Benzocyclobuten-1-ylmethyl)-4-piperidinecarboxylic acid 0.028 mole of 1-(iodomethyl)benzocyclobutene (Process 1, stage G}, 0.028 mole of 4-piperidinecarboxylic acid and 0.028 mole of triethylamine are mixed in 95 ml of dimethylformamide. The mixture is brought to 60° C. for 6 hours. It is evaporated to dryness, the residue is taken up with ethyl acetate and water and settling is allowed to take place.

The organic phase is dried over magnesium sulfate and concentrated. The residue is purified on a silica column using a mixture of toluene and methanol (95 : 5 V/V) as elution solvent.

Yield: 30%

Stage B 1-(Benzocyclobuten-1-ylmethyl)-4-(2,4-difluorobenzoyl) piperidine 0.025 mole of 1-(benzocyclobuten-1-ylmethyl)-4-piperidinecarbonyl chloride (prepared by the action of oxalyl chloride on the acid described above), dissolved in 50 ml of dichloromethane, is introduced into a suspension of 0.025 mole of 1,3-difluorobenzene and 0.026 mole of aluminum trichloride in 10 ml of dichloromethane. When the gaseous evolution has ceased, the mixture is hydrolyzed with ice, settling is allowed to take place and the product is extracted with 1 N hydrochloric acid. The aqueous phase is then alkalinized and extracted with dichloromethane. After evaporation of the solvent, the expected product is obtained.

Yield: 35%

Melting point: 70° C.

Proton nuclear magnetic resonance spectrum (solvent CDCl$_3$):

2.05–1.70 ppm, m, 4H; 2.2 ppm, m, 2H; 2.65 ppm, dd, 1H; 2.85 ppm, m, 2H 3.10 ppm, m, 3H; 3.4 ppm, dd. 1H; 3.7 ppm, m, 1H; 6.8,–7.3 ppm, m, 6H 7.9 ppm, m, 1H.

Stage C 1-(Benzocyclobuten-1-ylmethyl)-4-(2,4-difluorobenzoyl)piperidine oxime This compound was synthesized from the ketone described in stage B by applying the process described in stage E of Process No. 1. The compound was purified on a silica column using a mixture of dichloromethane and methanol (95:5 V/V) as eluent.

Proton nuclear magnetic resonance spectrum (solvent DMSO-$d_6$)

1.6–2.1 ppm, m, 4H; 2.1–2.6 ppm, m, 2H; 2.5–3.6 ppm, m, 7H; 3.7 ppm, m, 1H; 7.05–7.35 ppm, m, 7H; 10.95 ppm 1H exchangeable.

Stage D (RS)-3-[1-(Benzocyclobuten-1-ylmethyl)-4-piperidyl]-6-fluoro-1,2-benzisoxazole was synthesized from the oxime described above according to the method given in stage F of Process No. 1.

Process No. 3

Stage A 1-(Benzyocyclobuten-1-ylmethyl)-4-(2,4-difluorobenzoyl)-piperidine 0.0019 mole of4-(2,4-difluorobenzoyl)piperidine, 0.0019 mole of benzocyclobuten-1-ylmethyl para-toluenesulfonate and 0.04 mole of triethylamine dissolved in 50 ml of toluene are mixed and then brought to reflux for 18 hours. The reaction medium is then extracted with 1 N hydrochloric acid and the aqueous phase is alkalinized and extracted with dichloromethane. The oil obtained is purified on a silica column using a mixture of cyclohexane and acetone (93 : 7 V/V) as eluent.

Yield: 30%

Stage B

By applying the procedure described in Process No. 2, stages C and D, (RS)-3[1-(benzocyclobuten-1-ylmethyl)-4-piperidyl]-6-fluoro-1,2-benzisoxazole is obtained from the ketone described above.

EXAMPLE 2

(RS)-3-[1-[2-Benzocyclobuten-1-ylethyl)-4-piperidyl]-6-fluoro-1,2-benzisoxazole fumarate

Stage A

2-Benzocyclobuten-1-ylethanol

A three-necked flask is charged under a stream of nitrogen with 7.4 g of lithium aluminium hydride, and 70 ml of anhydrous tetrahydrofuran are then added. A solution of 2-benzocyclobuten-1-ylacetic acid (prepared according to the process described in J. Org. Chem., (1979), 44, p. 1036) in 120 ml of tetrahydrofuran is then introduced dropwise. The reaction solution is left stirring overnight. The flask is then cooled with an ice bath and the mixture is hydrolyzed by adding 6.6 ml of water, 6.6 ml of 4N sodium hydroxide and then 19.8 ml of water very gently. The complex is drained and washed with ethyl ether and the organic phase is dried over magnesium sulfate. After filtration, the filtrate is evaporated to dryness to obtain the expected compound.

Yield: 85%

Proton nuclear magnetic resonance spectrum (solvent CDCl$_3$):

1.5 ppm, 1H exchangeable; 2.0 ppm, g, 2H; 2.8 ppm, dd, 1H; 3.4 ppm, dd, 1H; 3.6 ppm, m, 1H; 3.85 ppm, t, 2H; 7.2 7.1 ppm, m+m, 2+2H.

Stage B

1-Bromo-2-benzocyclobuten-1-ylethane

A three-necked flask is charged with 9.6 g of the alcohol obtained above, dissolved in 13 ml of anhydrous benzene. 2.07 ml of phosphorous tribromide are then added slowly. The mixture is cooled to 0° C. and stirred for 30 minutes. It is then brought to reflux for 30 minutes. It is cooled and diluted with ethyl ether and the solution thereby obtained is poured into ice-cold water. Settling is allowed to take place and the organic phase is washed with saturated aqueous sodium chloride solution to neutrality. It is then dried over anhydrous magnesium sulfate, filtered and distilled to obtain the expected compound.

Yield: 63%

Proton nuclear magnetic resonance spectrum (solvent CDCl$_3$):

2.25 ppm, 2H; 2.8 ppm, dd, 1H; 3.4 ppm, dd, 1H; 3.5 ppm, t, 2H; 3.65 ppm, m, 1H; 7.3-7.0 ppm, m, 4H.

Stage C 2.8 ml of triethanolamine are added to a solution containing 4.4 g of 6-fluoro-3-piperid-4-yl-1,2-benzisoxazole in 80 ml of dimethylformamide, and 4.2 g of the compound obtained in the preceding stage are then added dropwise. The mixture is heated to 60° C. for 6 hours and then evaporated to dryness. The residue is taken up with 70 ml of ethyl ether and 30 ml of 1N hydrochloric acid. The precipitate formed is washed with ethyl ether. It is then taken up with 150 ml of ethyl acetate and with 50 ml of 1N sodium hydroxide. Settling is allowed to take place and the organic phase is washed to neutrality with saturated aqueous sodium chloride solution. It is dried over anhydrous magnesium sulfate and evaporated to obtain (RS)-3-[1-(2-benzocyclobuten-1-ylethyl)-4-piperidyl]-6-fluoro-1,2-benzisoxazole.

To prepare the fumarate, 1.87 g of fumaric acid, dissolved in 27 ml of ethanol, are poured into 5.65 g of the base dissolved in 5 ml of ethanol. The mixture is filtered and evaporated to dryness and the product is recrystallized in acetonitrile.

Melting point: 170°-190° C. (decomposition)

|  | Elemental analysis: | | |
|---|---|---|---|
|  | C % | H % | N % |
| Theory | 66.94 | 5.83 | 6.00 |
| Found | 67.25 | 5.96 | 6.35 |

EXAMPLE 3

(RS)-6-Fluoro-3-{1-[1-methylbenzocyclobuten-1-yl)methyl]-4-piperidyl}-1,2-benzisoxazole

Stage A

1-Iodomethyl-1-methylbenzocyclobutene 5.0 g of sodium iodide are added to a solution of 5.0 g of 1,1'-dimethylbenzocyclobutene tosylate (prepared according to the process described in J. Org. Chem., (1972), 32, p. 820) in 80 ml of acetone, and the expected compound is prepared according to the process described in Example 1, stage G.

Yield: 88%

Proton nuclear magnetic resonance spectrum (solvent CDCl$_3$):

1.55 ppm, s, 3H; 3.15 ppm, dd, 2H; 3.55 ppm, dd, 2H; 6.9 to 7.3 ppm, m, 4H.

Stage B (RS)-6-Fluoro-3-{1-[(1-methylbenzocyclobuten-1-yl)methyl]-4-piperidyl}-1,2-benzisoxazole hydriodide is prepared from the compound described in the preceding stage and 6-fluoro-3-(4-piperidyl)-1,2-benzisoxazole according to the process described in the final stage of Example 1. The residue is taken up with 1N hydrochloric acid and washed with ethyl ether. The mixture is then alkalinized with 1N sodium hydroxide and extracted with ethyl ether. The organic phase is washed with water, dried over anhydrous magnesium sulfate, filtered and evaporated to dryness. The product obtained is purified by flash chromatography using a mixture of dichloromethane and methanol (95 : 5 V/V) as eluent. To the base obtained, solubilized in ethyl ether, hydrochloric acid, dissolved in ethanol (3.5 N), is added.

The salt formed is recrystallized in a mixture of methanol and ethanol.

Yield: 14% Melting point: 215°-230° C.

|  | Elemental analysis | | | |
|---|---|---|---|---|
|  | C % | H % | N % | Halogen % |
| Theory | 68.30 | 6.25 | 7.24 | 9.16 |
| Found | 67.58 | 6.14 | 7.26 | 9.22 |

EXAMPLE 4

(RS)-3-[1-(2,3-Dihydro-2-benzofuranylmethyl)-4-piperidyl)]-6-fluoro-1,2-benzisoxazole

Stage A

2,3-Dihydro-2-benzofuranylmethanol

A three-necked flask is charged with 17 g of lithium aluminum hydride dissolved in anhydrous ethyl ether. 3 g of 2,3-dihydro-2-benzofurancarboxylic acid (Chim. Ler., (1973), 3, p. 259), dissolved in 1,140 ml of ethyl ether, are then introduced. The reaction medium is left stirring overnight. It is then hydrolyzed in an ice bath with 15.2 ml of water, 15.2 ml of 4N sodium hydroxide and then 45.2 ml of water. The complex is drained and washed with ethyl ether and the filtrate is dried and distilled to obtain the expected compound Yield: 90%

Proton nuclear magnetic resonance spectrum (solvent CDCl$_3$):

2.0 ppm, 1H exchangeable; 3.05 ppm, dd, 1H; 3.25 ppm, dd, 1H; 3.8 ppm, 2H; 4.9 ppm, 1H; 6.85 ppm, 2H; 7.15 ppm, d, 2H.

Stage B

2,3-Dihydro-2-benzofuranylmethyl para-toluenesulfonate

A three-necked flask is charged with 25.5 g of the alcohol obtained in the preceding stage and 170 ml of pyridine. 32.5 g of para-toluenesulfonyl chloride are added portionwise. The reaction medium is left stirring overnight at room temperature. It is evaporated to dryness and the residue is taken up with a mixture containing 900 ml of ethyl ether and 250 ml of 0.1N sulfuric acid. Settling is allowed to take place and the organic phase is washed with 0.1N sulfuric acid solution and then with a 10% strength solution of sodium hydrogen carbonate in water. The organic phase is dried over anhydrous magnesium sulfate and evaporated to dryness. The residue is recrystallized in cyclohexane.

Yield: 54%

Melting point: 69°-71° C.

Proton nuclear magnetic resonance spectrum (solvent CDCl$_3$):

2.5 ppm, s, 3H; 3.0 ppm, dd, 1H; 3.3 ppm, dd, 1H; 4.2 ppm, d, 2H; 4.95 ppm, m, 1H; 6.7 ppm, d, 1H; 6.85 ppm, 1H; 7.10 ppm, 1H; 7.15 ppm, d, 1H; 7.35 ppm, d, 2H; 7.8 ppm, d, 2H.

Stage C

2-Iodomethyl-2,3-dihydrobenzofuran 6.1 g of the product obtained in the preceding stage, 40 ml of anhydrous acetone and 4.5 g of sodium iodide are brought to reflux for 2 hours. The reaction medium is poured into 50 ml of water and 50 ml of ethyl ether. Settling is allowed to take place and the aqueous phase is extracted several times with ethyl ether. The ether extracts are washed with 0.5N sodium thiosulfate and then with water saturated with sodium chloride. The organic phase is dried over anhydrous magnesium sulfate and evaporated to dryness to obtain the expected compound.

Yield: 96%

Stage D

To obtain (RS)-3-[1-(2,3-dihydro-2-benzofuranylmethyl)-4-piperidyl]-6-fluoro-1,2-benzisoxazole, 5 g of the compound obtained in the preceding stage are reacted with 3.65 g of 6-fluoro-3-piperid-4-yl-1,2-benzisoxazole in the presence of 2.4 ml of triethanolamine according to the process described in the final stage of Example 1.

The solid obtained is taken up with 100 ml of 1N hydrochloric acid and 50 ml of ethyl ether. The precipitate formed is drained and taken up with 150 ml of ethyl ether and 100 ml of 1N sodium hydroxide. Settling is allowed to take place and the organic phase is washed to neutrality with water saturated with sodium chloride. It is dried over magnesium sulfate and evaporated to dryness and the residue obtained is recrystallized in ethyl acetate.

Yield: 33%

Melting point: 115°-117° C.

|  | Elemental analysis | | |
|---|---|---|---|
|  | C % | H % | N % |
| Theory | 71.57 | 6.01 | 7.95 |
| Found | 71.48 | 6.06 | 7.99 |

EXAMPLE 5

(RS)-6-Fluoro-3-[1-(7-methoxy-2,3-dihydro-2-benzofuranylmethyl-4-piperidyl]-1,2-benzisoxazole

Stage A

2-Allyloxy-1-methoxybenzene 124 g of 2-methoxyphenol and 152 g of potassium carbonate in 500 ml of dimethylformamide are brought to 60° C. with stirring for 30 minutes. 127 g of allyl bromide are introduced and the reaction medium is then left at 60° C. for 1 hour. It is diluted with 2 l of water and extracted with ethyl ether and the organic phase is washed with sodium hydroxide. The organic phase is dried and the ether evaporated off. The product is then distilled at 115° C. and at 20 mmHg to obtain 129.6 g of the expected compound.

Yield: 79.5%

Proton nuclear magnetic resonance spectrum (solvent CDCl$_3$):

3.8 ppm, s, 3H; 4.55 ppm, m, 2H; 5.1 to 5.5 ppm, m, 2H; 4.4 to 5.75 ppm, m, 1H; 6.85 ppm, m, 4H.

Stage B

2-Allyl-6-methoxyphenol 129 g of the compound obtained in the preceding stage are brought to 230° C. for one hour. The medium is taken up with 500 m of ethyl ether and washed with 2.5N sodium hydroxide and then with water. The organic phase is dried and then evaporated. The residue is distilled at 145° C. and at 24 mmHg to obtain the expected compound.

Yield: 96%

Proton nuclear magnetic resonance spectrum (solvent CDCl$_3$):

3.4 and 3.3 ppm, m+m, 2H; 3.85 ppm, s, 3H; 4.0 ppm, m, 1H; 5.05 ppm, m, 2H; 5.7 to 5.5 ppm, 1H exchangeable; 6.9 to 6.65 ppm, m, 3H.

Stage C

7-Methoxy-2,3-dihydro-2-benzofuranylmethanol 124 g of 2-allyl-6-methoxyphenol, dissolved in 80 ml of acetic acid, are added to a mixture, cooled to 15° C., containing 160 ml of 32% strength peracetic acid in acetic acid and 2.4 g of sodium acetate. The mixture is left at room temperature for 48 hours and then hydrolyzed with 2 l of water containing 400 g of sodium carbonate. The mixture is extracted with ethyl ether and the organic phase is washed with sodium hydroxide. It is dried, the ether is evaporated off and the residue is distilled at 110° C. and at 0.02 mmHg to obtain 7-methoxy-2,3-dihydro-2-benzofuranylmethanol.

Yield: 16%

Proton nuclear magnetic resonance spectrum (solvent CDCl$_3$):

2.1 ppm, 1H exchangeable; 3.0 to 3.3 ppm, m, 2H; 3.7 to 4.0 ppm, m+s, 2H+3H; 5.0 ppm, m, 1H; 6.7 ppm, m, 3H.

Stage D

7-Methoxy-2,3-dihydro-2-benzofuranylmethyl tosylate 22.8 g of para-toluenesulfonyl chloride are added portionwise to 22 g of the alcohol obtained in the preceding stage, dissolved in 100 ml of pyridine. The procedure then follows the method described in Example 4, stage B, using ethyl acetate as an organic extraction solvent.

Yield: 85%

Melting point: 108°–110° C.

Proton nuclear magnetic resonance spectrum (solvent CDCl$_3$):

2.5 ppm, s, 3H; 3.1 ppm, m, 1H; 3.4 ppm, m, 1H; 3.9 ppm, s, 3H; 4.2 ppm, m, 2H; 5.0 ppm, m, 1H; 6.8 ppm, m, 3H; 7.3 ppm, d, 2H; 7.8 ppm, d, 2H.

Stage E

2-Iodomethyl-7-methoxy-2,3-dihydrobenzofuran

This compound was obtained according to the process described in Example 4, stage C, from 7-methoxy-2,3-dihydro-2-benzofuranylmethyl tosylate and sodium iodide.

Yield 95%

Proton nuclear magnetic resonance spectrum (solvent CDCl$_3$):

3.2 to 3.5 ppm, m, 2H; 3.0 to 3.6 ppm, m, 2H; 3.9 ppm, s, 3H; 5.09 ppm, m, 1H; 6.8 ppm, m, 3H.

Stage F (RS)-6-Fluoro-3-[1-(7-methoxy-2,3-dihydro-2-benzofuranylmethyl)-4-piperidyl]-1,2-benzisoxazole is obtained from 2-iodomethyl-7-methoxy-2,3-dihydrobenzofuran and 6-fluoro-3-piperid-4-yl-1,2-benzisoxazole according to the process described in Example 4, stage D.

Yield: 31.5%

Melting point: 120°–122° C.

| | Elemental analysis: | | |
| --- | --- | --- | --- |
| | C % | H % | N % |
| Theory | 69.09 | 6.06 | 7.32 |
| Found | 68.90 | 6.00 | 7.55 |

EXAMPLE 6

(RS)-6-Fluoro-3-[1-(5-fluoro-2,3-dihydro-2-benzofuranylmethyl)-4-piperidyl]-1,2-benzisoxazole

Stage A

1-Allyloxy-4-fluorobenzene

This compound was prepared from 4-fluorophenol and allyl bromide according to the process described in Example 5, stage A. The solvent used is acetone and the reaction was carried out in the presence of sodium hydroxide.

Yield: 75%

Proton nuclear magnetic resonance spectrum (solvent CDCl$_3$):

4.5 ppm, m, 2H; 5.15 to 5.55 ppm, m, 2H; 5.6 to 6.5 ppm, m, 1H; 4.65 to 7.1 ppm, m, 4H.

Stage B

2-Allyl-4-fluorophenol

This compound was obtained from 1-allyloxy-4-fluorobenzene according to the process described in Example 5, stage B.

Yield: 86%

Proton nuclear magnetic resonance spectrum (solvent CDCl$_3$):

3.4 ppm, m, 2H; 5.1 ppm, 1H exchangeable; 4.95 to 5.4 ppm, m, 2H; 5.7 to 6.4 ppm, m, 1H; 6.6 to 7.1 ppm, m, 3H.

Stage C

5-Fluoro-2,3-dihydro-2-benzofuranylmethanol

This compound was prepared from the phenol obtained in the preceding stage according to the process described in Example 5, stage C.

Yield: 46%

Proton nuclear magnetic resonance spectrum (solvent CDCl$_3$);

2.0 ppm, 1H exchangeable; 2.9 to 3.3 ppm, m, 2H; 3.6 to 3.9 ppm, m, 2H; 5.0 ppm, m, 1H; 6.5 to 6.9 ppm, m, 3H.

Stage D

5-Fluoro-2,3-dihydro-2-benzofuranylmethyl tosylate

Using the process described in Example 5, stage D, the expected compound is obtained from 5-fluoro-2,3-dihydro-2-benzofuranylmethanol.

Yield: 83%

Melting point: >50° C.

Proton nuclear magnetic resonance spectrum (solvent CDCl$_3$):

2.45 ppm, s, 3H; 3.0 ppm, m, 1H; 3.3 ppm, m, 1H; 4.15 ppm, d, 2H; 4.95 ppm, m, 1H; 6.5 to 6.9 ppm; m, 3H; 7.8 ppm, d, 2H; 7.75 ppm, d, 2H.

Stage E

5-Fluoro-2-iodomethyl-2,3-dihydrobenzofuran

This compound was obtained from 5-fluoro-2,3-dihydro-2-benzofuranylmethyl tosylate according to the process described in Example 4, stage C.

Yield: 96%

Proton nuclear magnetic resonance spectrum (solvent CDCl$_3$):

3.0 ppm, m, 1H; 3.2 to 3.5 ppm, m, 3H; 4.9 ppm, m, 1H; 6.5 to 6.9 ppm, m, 3H.

Stage F (RS)-6-Fluoro-3-[1-(5-fluoro-2,3-dihydro-2-benzofuranylmethyl)-4-piperidyl]-1,2-benzisoxazole is obtained from the compound prepared in the preceding stage according to the process described in Example 4, stage D.

Yield: 11%

Melting point: 129°–130° C.

| Elemental analysis: | | | |
|---|---|---|---|
| | C % | H % | N % |
| Theory | 68.10 | 5.44 | 7.56 |
| Found | 67.84 | 5.61 | 7.76 |

EXAMPLE 7

(RS)-6-Fluoro-3-{1-(2-benzofuranylmethyl)-4-piperidyl]-1,2-benzisoxazole hydrochloride

Stage A

2-Benzofuranylmethanol

This compound was prepared from ethyl 2-benzofurancarboxylate (J.A.C.S., (1951), 73, p. 872) according to the process described in Example 4, stage A.

Yield: 85%

Proton nuclear magnetic resonance spectrum (solvent $CDCl_3$):

2.15 ppm, 1H exchangeable, 4.8 ppm, s, 2H; 6.65 ppm, s, 1H; 7.20 to 7.35 ppm, m, 2H; 7.5 ppm, dd, 1H; 7.6 ppm, dd, 1H.

Stage B 2-(Chloromethyl)benzofuran

A three-necked flask is charged with 33.2 g of 2-benzofuranylmethanol dissolved in 450 ml of anhydrous chloroform, 48.8 ml of thionyl chloride are then introduced dropwise and the temperature is raised gently to reflux and maintained for 3 hours 30 minutes. The reaction medium is then cooled and poured into 1 l of water, and is thereafter diluted with 500 ml of dichloromethane. After settling has taken place, the organic phase is washed to neutrality and dried over anhydrous magnesium sulfate, the solvent is evaporated off and the residue is distilled under vacuum to obtain the expected compound.

Yield: 80%

Proton nuclear magnetic resonance spectrum (solvent $CDCl_3$):

4.7 ppm, s, 2H; 6.75 ppm, 1H; 7.25 ppm, td, 1H; 7.3 ppm, td, 1H; 7.5 ppm, d, 1H; 7.6 ppm, dd, 1H.

Stage C (RS)-6-Fluoro-3-[1-(2-benzofuranylmethyl)-4piperidyl]-1,2-benzisoxazole is prepared according to the process described in Example 1, from 2-(chloromethyl)benzofuran and 6-fluoro-3-(4-piperidyl)-1,2-benzisoxazole.

Yield: 54%

To obtain the corresponding hydrochloride, the base is dissolved in acetonitrile, and a suitable quantity of hydrochloric acid, dissolved in ethyl ether, is then added. After evaporation of the solvent, the expected salt is obtained, and is then recrystallized in acetonitrile.

Melting point: Decomposition from 190° C.

| Elemental analysis: | | | | |
|---|---|---|---|---|
| | C % | H % | N % | Cl % |
| Theory | 65.20 | 5.21 | 7.24 | 9.16 |
| Found | 64.90 | 5.50 | 7.48 | 9.18 |

EXAMPLE 8

6-Fluoro-3-[1-(4-oxo-4H-chloromen-2-ylmethyl)-4-piperidyl]-1,2-benzisoxazole hydrochloride

Stage A

2-Methylthiomethyl-4-oxo-4H-chromene

A mixture containing 14.3 g of 2-hydroxyacetomlphenone and 28.3 g of ethyl methylthioacetate in 25 ml of tetrahydrofuran is added rapidly to 20 g of 50% strength sodium hydride suspended in 15 ml of tetrahydrofuran. The mixture is then brought to reflux for 30 min. It is hydrolyzed under a stream of nitrogen with 500 ml of water, 500 ml of methanol and 70 ml of concentrated hydrochloric acid are added and the mixture is brought to reflux for one hour. The methanol is evaporated off, the residue is extracted with ethyl ether, the organic phase is washed with sodium hydroxide and the solvent is evaporated off to obtain the expected product.

Yield: 38%

Melting point: 77°–79° C.

Proton nuclear magnetic resonance spectrum (solvent $CDCl_3$);

2.2 ppm, s, 3H; 3.6 ppm, s, 2H; 6.3 ppm, s, 1H; 7.3 to 7.5 ppm, m, 2H; 7.7 ppm, m, 1H; 8.2 ppm, dd, 1H.

Stage B

2-Iodomethyl-4-oxo-4H-chromene 8 g of 2-methylthiomethyl-4-oxo-4H-chromene, 200 ml of methyl iodide and 26 ml of dichloromethane are brought to reflux with stirring for 4 days. The precipitate is filtered off, the excess solvents and reagents are evaporated off, the residue is taken up with ethyl ether and the organic phase is washed with sodium thiosulfate solution, dried and evaporated.

Yield: 83%

Melting point: 144°–146° C.

Proton nuclear magnetic resonance spectrum (solvent $CDCl_3$):

4.25 ppm, s, 2H; 6.35 ppm, s, 1H; 7.3 to 7.5 ppm, m, 2H; 7.65 ppm, td, 1H; 8.15 ppm, dd, 1H.

Stage C

6-Fluoro-3-[1-(4-oxo-4H-chromen-2-ylmethyl]-4-piperidyl]-1,2-benzisoxazole is obtained by condensation of the compound obtained in the preceding stage with 6-fluoro-3-piperid-4-yl-1,2-benzisoxazole according to the process described in the final stage of Example 1. The hydrochloride is obtained after the addition of a suitable quantity of N hydrochloric acid. Recrystallization in methanol.

Yield: 38%

Melting point: >260° C.

| Elemental analysis: | | | | |
|---|---|---|---|---|
| | C % | H % | N % | Cl % |
| Theory | 63.69 | 4.86 | 6.75 | 8.55 |
| Found | 63.27 | 5.12 | 6.79 | 8.59 |

EXAMPLE 9

3-[1-{[1,2-Dihydro-2-oxo-1-(3-trifluoromethylphenyl)-1,8-naphthyridin-3-yl]ethyl}-4-piperidyl]-6-fluoro-1,2-benzisoxazole hydrochloride

Stage A

2-[(3-Trifluoromethylphenyl)amino-3-pyridylmethanol 500 ml of anhydrous ethyl ether are run gently onto 26 g of lithium aluminum hydride, and 100 g of niflumic acid, dissolved in 250 ml of anhydrous tetrahydrofuran, are then added dropwise. The mixture is then brought to reflux for 3 hours. After cooling, it is hydrolyzed with 150 ml of ethyl acetate and 100 ml of saturated sodium sulfate solution. After filtration, the filtrate is concentrated to obtain the expected compound in the form of a yellow solid.

Yield: 85%

Melting point: 102° C.

Proton nuclear magnetic resonance spectrum (solvent $CDCl_3$):

2.1 ppm, 1H exchangeable, 4.7 ppm, s, 2H; 6.75 ppm, dd, 1H; 7.15 to 7.5 ppm, m, 3H; 7.75 ppm, d, 1H; 7.85 ppm, 1H exchangeable; 7.9 ppm, s, 1H; 8.25 ppm, dd, 1H.

Stage B

2-[(3-Trifluoromethylphenyl)amino]-3-pyridinecarbaldehyde 260 g of manganese oxide are added to 80 g of the alcohol prepared above, dissolved in one liter of chloroform, and the mixture is left to react for approximately 48 hours at room temperature. It is then filtered through Celite, the residue is washed with methylene chloride and the filtrate is concentrated. The residue obtained is recrystallized in heptane.

Yield: 54%

Melting point: 76° C.

Proton nuclear magnetic resonance spectrum (solvent $CDCl_3$):

6.95 ppm, dd, 1H; 7.35 ppm, d, 1H; 7.45 ppm, 1H; 7.9 ppm, dd+m, 2H; 8.2 ppm, s, 1H; 8.5 ppm, dd, 1H; 9.95 ppm, s, 1H; 10.6 ppm, s, 1H.

Stage C

2-[1,2-Dihydro-2-oxo-1-(3-trifluoromethylphenyl)-1,8-naphthyridin-3-yl]ethanol

A mixture containing 20 g of the compound prepared in the preceding stage and 20 g of γ-butyrolactone in 100 ml of benzene is introduced into a suspension containing 4.6 g of sodium hydride (60% strength) in 100 ml of benzene. After the introduction is complete, the mixture is left overnight at room temperature and then hydrolyzed with 50 ml of water. After settling has taken place, the organic phase is washed several times with water, dried and concentrated to obtain the expected compound.

Yield: 69%

Melting point: 176° C.

Proton nuclear magnetic resonance spectrum (solvent $CDCl_3$):

2.7 ppm, 1H exchangeable; 2.95 ppm, t, 2H; 3.95 ppm, q, 2H; 7.2 ppm, dd, 1H; 7.5 ppm, dd, 1H; 7.6 ppm, s, 1H; 7.65 to 7.8 ppm, m, 3H; 7.95 ppm, dd, 1H; 8.4 ppm, dd, 1H.

Stage D

1-Chloro-2-[1,2-dihydro-2-oxo-1-(3-trifluoromethylphenyl)-1,8-naphthyridin-3-yl]ethane This compound was prepared from the compound obtained in the preceding stage according to the process described in Example 7, stage B.

Yield: 92%

Stage E 3.5 g of the compound obtained in stage D, 2.18 g of the compound obtained in stage F of Example 1 and 1.73 ml of N,N-diisopropylethylamine dissolved in 70 ml of dimethylformamide are brought to 60° C. for 30 hours. The reaction medium is then concentrated, the residue is taken up with ethyl acetate and the organic phase is extracted with N hydrochloric acid. The precipitate formed is filtered off and washed with ethyl ether. It is recrystallized in methanol to obtain the expected compound.

Yield: 92%

Melting point: 143°-147° C.

| | Elemental analysis: | | | |
|---|---|---|---|---|
| | C % | H % | N % | Cl % |
| Theory | 60.79 | 4.40 | 9.78 | 6.19 |
| Found | 60.76 | 4.26 | 9.81 | 6.29 |

EXAMPLE 10

(RS)-3-[1-(5-Chlorobenzocyclobuten-1-ylmethyl)-4-piperidyl]-6-fluoro-1,2-benzisoxazole This compound was obtained from 5-chloro-1-(iodomethyl)benzocyclobutene (prepared from 5-chloro-1-(cyanomethyl)benzocyclobutene described in J. Org. Chem (1968) 33 (8) p. 3327) and 6-fluoro-3-piperid-4-yl-1,2-benzisoxazole according to the process described in Example 1, stage H, Process 1.

Yield: 8%

Melting point: 115°-116° C.

| | Elemental analysis: | | | |
|---|---|---|---|---|
| | C % | H % | N % | Cl % |
| Theory | 68.01 | 5.44 | 7.55 | 9.56 |
| Found | 68.41 | 5.56 | 7.59 | 9.52 |

EXAMPLE 11

(RS)-6-Fluoro-3-[1-(7-isopropyl-2,3-dihydro-2-benzofuranylmethyl)-4-piperidyl]-1,2-benzisoxazole This compound was obtained in base form according to the process described in Example 5, but using 2-isopropylphenol in stage A instead of 2-methoxyphenol.

Yield: 12% (final stage)

To obtain the corresponding fumarate, the base is dissolved in a suitable quantity of a 2% strength ethanolic solution of fumaric acid. The solution is chilled and the precipitate formed is filtered off to obtain the expected salt.

Melting point: 206°-208° C.

| | Elemental analysis: | | |
|---|---|---|---|
| | C % | H % | N % |
| Theory | 65.87 | 6.12 | 5.49 |

-continued

| | Elemental analysis: | | |
|---|---|---|---|
| | C % | H % | N % |
| Found | 65.70 | 6.00 | 5.23 |

EXAMPLE 12

(RS)-3-[1-(7-Fluoro-2,3-dihydro-2-benzofuranylmethyl)-4-piperidyl]-6-fluoro-1,2-benzisoxazole This compound was obtained according to the process described in Example 5, but using 2-fluorophenol in stage A instead of 2-methoxyphenol.

Yield: 15% (final stage)

Melting point: 126°–128° C.

| | Elemental analysis: | | |
|---|---|---|---|
| | C % | H % | N % |
| Theory | 68.10 | 5.44 | 7.56 |
| Found | 67.88 | 5.49 | 7.53 |

EXAMPLE 13

(RS)-6-Fluoro-3-[1-(3,4-Methylenedioxybenzocyclobuten-1-ylmethyl)-4-piperidyl]-1,2-benzisoxazole fumarate

Stage A

2-Cyano-3-(2,3-methylenedioxyphenyl)acrylic acid 0.13 mole of 2,3-methylenedioxybenzaldehyde, 0.13 mole of cyanoacetic acid and 0.022 mole of ammonium acetate are mixed in 18.6 ml of pyridine and 118 ml of benzene. The mixture is brought to reflux until a volume of water equal to 2.4 ml is obtained. The mixture is left overnight at room temperature, the precipitate formed is filtered off and the filtrate is concentrated.

The precipitate and the evaporated filtrate are taken up in water and acidified with 18% strength hydrochloric acid. The mixture is filtered. The product obtained is crystallized in acetic acid.

Yield: 44%

Melting point: 230° C. (sublimation)

Proton nuclear magnetic resonance spectrum (solvent DMSO-$d_6$):

3.5 ppm, broad s, 1H; 6.2 ppm, s, 2H; 7.0 ppm, t, 1H; 7.15 ppm, d, 1H; 7.7 ppm, d, 1H; 8.2 ppm, s, 1H.

Stage B

2-Cyano-3-(2,3-methylenedioxyphenyl)propionic acid 0.055 mole of the acid obtained in the preceding stage is mixed in 129 ml of methanol and 43 ml of saturated aqueous sodium bicarbonate solution. 0.17 mole of sodium borohydride is added at 18° C. The mixture is then allowed to return to room temperature.

The reaction medium is concentrated and acidified (pH 1) using hydrochloric acid. It is extracted with ethyl ether. The organic phases are washed with water to neutrality. They are dried.

The expected compound is obtained.

Yield: 82%

Melting point: 118° C.

Proton nuclear magnetic resonance spectrum (solvent DMSO-$d_6$):

3.1 ppm, dd, 1H; 3.3 ppm, dd, 1H; 3.85 ppm, dd, 1H; 6 ppm, m, 2H; 6.8 ppm, m, 3H; 8.8 ppm, broad s, 1H.

Stage C

1-Cyano-2-(2,3-methylenedioxyphenyl)ethane 0.046 mole of the acid obtained in stage B is mixed with 19 ml of dimethylformamide and the mixture is then heated to 150° C. for 2 hours. The mixture is taken up with water and the product is extracted with ethyl ether. The organic phases are washed with sodium bicarbonate solution and then with water; they are dried and the solvent is evaporated off to obtain an oily residue.

Yield: 83%

Proton nuclear magnetic resonance spectrum (solvent CDCl$_3$):

2.65 ppm, t, 2H; 2.95 ppm, t, 2H; 5.95 ppm, s, 2H; 6.65–6.9 ppm, m, 3H.

Stage D

1-Cyano-2-(6-bromo-2,3-methylenedioxyphenyl)ethane 0.31 mole of the nitrile described in stage C is dissolved in 179 ml of acetic acid. A solution of bromine (0.32 mole in 35 ml of acetic acid) is introduced dropwise at 18° C. into this solution. The mixture is left overnight at room temperature. It is hydrolyzed with a mixture of potassium acetate, water and ice. It is extracted with ethyl ether and the ether phase is then washed several times with water.

The compound obtained is purified on a silica column using a mixture of cyclohexane and dichloromethane (20 : 80 V/V) as eluent.

Yield: 42%

Proton nuclear magnetic resonance spectrum (solvent CDCl$_3$):

2.65 ppm, t, 2H; 3.05 ppm, t, 2H; 6 ppm, s, 2H; 6.65 ppm, d, 1H; 7 ppm, d, 1H.

Stage E

1-Cyano-3,4-methylenedioxybenzocyclobutane

The amide is prepared by introducing 0.16 gram-atom of sodium in lumps into 45 ml of liquid ammonia containing 0.12 g of potassium ferricyanide hexahydrate and 0.12 g of ferric nitrate.

The compound obtained in the preceding stage is then added rapidly, the reactants are left in contact and decomposition is carried out by adding 6.9 g of ammonium chloride slowly. The mixture is left overnight and then extracted with ethyl ether and the organic phase is washed several times with water.

The compound thereby obtained is purified on a silica column using a mixture of dichloromethane and cyclohexane (50 : 50 V/V) as eluent.

Yield: 49%

Melting point: 85° C.

Proton nuclear magnetic resonance spectrum (solvent CDCl$_3$):

3.55 ppm, 2H; 4.2 ppm, 1H; 5.95 ppm, 2H; 6.6–6.9 ppm, 2d, 2H.

Stage F 2,3-Methylenedioxybenzocyclobutene-1-carboxylic acid 0.0335 mole of the compound obtained in stage E in a mixture of alcoholic potassium hydroxide (6.71 g of potassium hydroxide in 47.6 ml of ethanol) is mixed and left stirring overnight at room temperature. 9 ml of water are then added and the mixture is brought to reflux for 4 hours. It is concentrated.

The residue is taken up with water and the aqueous phase is washed several times with ethyl ether, acidified with hydrochloric acid and then extracted with ethyl ether to obtain the expected compound.

Yield: 98%

Melting point: 125° C.

Proton nuclear magnetic resonance spectrum (solvent $CDCl_3$):

3.45 ppm, d, 2H; 4.3 ppm, t, 1H; 5.95 ppm, 2H; 6.7 ppm, 2d, 2H.

Stage G 2,3-Methylenedioxybenzocyclobuten-1-ylmethanol

This compound was prepared from the acid obtained above according to the process described in Example 2, stage A.

Yield: 87%

Proton nuclear magnetic resonance spectrum (solvent $CDCl_3$):

1.5 ppm, 1H exchangeable; 2.9 ppm, dd, 1H; 3.25 ppm, dd, 1H; 3.65 ppm, 1H; 3.9 ppm, m, 2H; 5.9 ppm, s, 2H; 6.65 ppm, 2d, 2H.

Stage H 2,3-Methylenedioxybenzocyclobuten-1-ylmethyl paratoluenesulfonate 0.1 mole of p-toluenesulfonyl chloride is added at 0° C. to 0.07 mole of the alcohol described above, dissolved in 84 ml of pyridine. The mixture is left at room temperature. It is concentrated and the residue is taken up with water. The precipitate formed is filtered off and washed with water and then with N hydrochloric acid.

Yield: 82%

Melting point: 102° C.

Proton nuclear magnetic resonance spectrum (solvent ($DMSO-d_6$):

2.4 ppm, s, 3H; 2.7–2.8 ppm, 2d, 1H; 3.1–3.3 ppm, 2d, 1H; 3.7 ppm, 1H; 4.25 ppm, 2H; 5.95 ppm, 2H; 6.55 ppm, d, 1H; 6.75 ppm, d, 1H; 7.45 ppm, d, 2H; 7.75 ppm, d, 2H.

Stage I 0.01 mole of the compound obtained in stage H is mixed with 0.02 mole of 6-fluoro-3-piperid-4-yl-1,2-benzisoxazole, dissolved in 50 ml of toluene, and the mixture brought to reflux for 12 hours. It is taken up with a mixture of water and ethyl ether. The ether phase is washed repeatedly several times with water.

The (RS)-6-fluoro-3-[1-(3,4-methylenedioxybenzocyclobuten-1-ylmethyl)-4-piperidyl]-1,2-benzisoxazole thereby obtained in the form of an oil is purified on a silica column using a mixture of dichloromethane and ethyl acetate (90 : 10 V/V) as eluent.

Yield: 37%

The product is then salified with a solution of fumaric acid in methanol to obtain the expected salt.

Melting point: 185°–188° C.

| | Elemental analysis: | | |
|---|---|---|---|
| | C % | H % | N % |
| Theory | 62.90 | 5.08 | 5.64 |
| Found | 62.85 | 4.94 | 5.45 |

EXAMPLE 14

3-}1-[(1,2-Dihydro-2-oxo-1-phenyl-1,8-naphthyridin-3-yl)ethyl]-4-piperidyl}-6-fluoro-1,2-benzisoxazole

Stage A 2-(Phenylamino)nicotinic acid 50 ml of distilled aniline and 43.2 g of 2-chloronicotinic acid are mixed in 126 ml of xylene. The mixture is brought to reflux for 4 hours. It is allowed to cool and the precipitate is filtered off and washed several times with water.

Yield: 74%

Melting point: 148° C.

Proton nuclear magnetic resonance spectrum (solvent $CDCl_3$):

6.8 ppm, dd, 1H; 7.1 ppm, t, 1H; 7.35 ppm, t, 2H; 7.5 ppm, d, 2H; 8.35 ppm, dd, 2H; 9.8 and 10.6 ppm, 2H exchangeable.

Stage B (RS)-3-(1-[(1,2-Dihydro-2-oxo-1-phenyl-1,8-naphthyridin-3-yl)ethyl]-4-piperidyl}-6-fluoro-1,2-benzisoxazole was obtained according to the process described in Example 9 (stages A to E), but using 2(phenylamino)-nicotinic acid in stage A instead of niflumic acid.

Yield: 14% (final stage)

Melting point: 203°–206° C.

| | Elemental analysis: | | |
|---|---|---|---|
| | C % | H % | N % |
| Theory | 71.78 | 5.38 | 11.96 |
| Found | 71.78 | 5.53 | 11.94 |

EXAMPLE 15

3-[1-{[1.2-Dihydro-2-oxo-1-(2-fluorophenyl)-1.8-naphthyridin-3-yl]ethyl)-4-piperidyl-6-fluoro-1.2-benzisoxazole

Stage A

2-[(2-Flurochenyl)amino]nicotinic acid

This compound was prepared according to the process described in Example 14, stage A, but using 2-fluoroaniline instead of aniline.

Yield: 80%

Melting point: 144° C.

Proton nuclear magnetic resonance spectrum (solvent $DMSO-d_6$):

6.8 to 7.4 ppm, m, 5H; 8.1 to 8.6 ppm, m+exchangeable, 2H+1H; 10.65 ppm, 1H exchangeable.

Stage B

2-[(2-Fluorophenyl)amino]-3-pyridinecarbaldehyde

This compound was obtained from the acid described in the preceding stage according to the process described in Example 9, stages A and B.

Yield: 18%

Melting point: 94° C.

Proton nuclear magnetic resonance spectrum (solvent $CDCl_3$):

6.9 ppm, dd, 1H; 7.2–7 ppm, m, 3H; 7.9 ppm, dd, 1H; 8.45 ppm, dd, 1H; 8.55 ppm, dd, 1H; 9.95 ppm, s, 1H; 10.6 ppm, s, 1H.

Stage C

Ethyl 3-[1-(6-fluoro-1,2-benzisoxazol-3-yl)-1piperidyl]propionate 0.045 mole of 6-fluoro-3-piperid-1-yl-1,2-benzisoxazole is dissolved in 15 ml of ethanol. 6.2 ml of ethyl acrylate, dissolved in 15 ml of ethanol, are then introduced and the mixture is left stirring overnight. It is concentrated, the residue is taken up with water and the aqueous phase is extracted with ethyl ether.

Yield: 95%

Melting point: 58°–59 C.

Proton nuclear magnetic resonance spectrum (solvent $CDCl_3$):

1,3 ppm, t, 3H; 2.3–2.0 ppm, 6H; 2.55 ppm, t, 2H; 2.75 ppm, t, 2H; 3.05 ppm, 3H; 4.15 ppm, c, 2H; 7.05 ppm, dd, 1H; 7.25 ppm, dd, 1H; 7.7 ppm, dd, 1H.

Stage D 0.015 mole of sodium hydride, 0.01 mole of the compound obtained in stage C and 0.01 mole of the compound obtained in stage B are covered with 20 ml of benzene. Before the introduction of the latter is begun, the reaction is initiated with a few drops of ethanol. The mixture is left stirring at room temperature overnight and filtered.

Recrystallization in dichloromethane.

Yield: 11%

Melting point: 255°–259° C.

|  | Elemental analysis: | | |
|---|---|---|---|
|  | C % | H % | N % |
| Theory | 68.64 | 4.69 | 11.86 |
| Found | 68.50 | 4.62 | 11.84 |

EXAMPLE 16

6-Fluoro-3-[1-(2-indanyl)-4-piperidyl[-1,2-benzisoxazole 0.173 mole of 2-indanyl para-toluenesulfonate (prepared from 2-indanol according to the procedure described in Example 4, stage B), 0.173 mole of 6-fluoro-3-piperid-4-yl-1,2-benzisoxazole, dissolved in 50 ml of toluene, and 0.0346 mole of triethylamine are mixed.

The mixture is brought to reflux for 12 hours. The cloudiness is removed by filtration. The toluene is separated after settling has taken place and washed with water. The product is purified on a silica column using dichloromethane as solvent.

Yield: 16%

Melting point: 153°–155° C.

|  | Elemental analysis: | | |
|---|---|---|---|
|  | C % | H % | N % |
| Theory | 74.98 | 6.29 | 8.33 |
| Found | 74.91 | 6.54 | 8.35 |

EXAMPLE 17

(RS)-3-[1-(3-chlorobenzocyclobuten-1-ylmethyl)-4-piperidyl]-6-fluoro-1,2-benzisoxazole hydrochloride

Stage A

3-Chlorobenzocyclobutene-1-carboxylic acid 5.0 g of 3-chloro-1-cyanobenzocyclobutane (prepared according to the process described in Patent EP 119,107) are added to a solution of 6.0 g of potassium hydroxide in 58 ml of ethanol The mixture is stirred at room temperature overnight. 7.5 ml of water are then added and the mixture is heated to reflux for 6 hours. The ethanol is evaporated off to dryness. The residue is taken up with water and the aqueous phase is washed with ethyl ether, then acidified (pH 1) with 1N hydrochloric acid and extracted with dichloromethane. The organic phase is dried, filtered and evaporated to dryness.

Yield: 95%

Melting point: 106° C.

Proton nuclear magnetic resonance spectrum (solvent $CDCl_3$): 3.5 ppm, d, 2H; 4.3 ppm, t, 1H; 7.4 to 6.9 ppm, m, 3H.

Stage B

3-Chlorobenzocyclobuten-1-ylmethanol

This compound was prepared from the acid described in stage A according to the process described in Example 2, stage A.

Yield: 86%

Proton nuclear magnetic resonance spectrum (solvent $CDCl_3$):

1.8 ppm, m, 1H exchangeable; 2.9 ppm, m, 1H; 3.3 ppm, m, 1H; 4.1 to 3.5 ppm, m, 3H; 7.3 to 6.9 ppm, m, 3H.

Stage C

3-Chloro-1-(iodomethyl)benzocyclobutene

This compound was obtained from the alcohol described in the preceding stage according to the process described in Example 4, stages B and C.

Yield: 61%

Proton nuclear magnetic resonance spectrum (solvent $CDCl_3$):

2.85 ppm, 1H; 3.5 ppm, 3H; 3.9 ppm, 1H; 7.2 ppm, m, 3H.

Stage D (RS)-3-[1-(3-Chlorobenzocyclobuten-1-ylmethyl)-4-piperidyl]-6-fluoro-1,2-benzisoxazole was prepared according to the process described in Example 1, stage H, but replacing 1-(iodomethyl)benzocyclobutene by 3-chloro- 1-(iodomethyl)benzocyclobutene.

Yield: 15%

The corresponding hydrochloride was obtained after the addition of a suitable quantity of ethanolic hydrogen chloride and recrystallization in ethyl acetate.

Melting point: 205°–209° C.

|  | Elemental analysis: | | | |
|---|---|---|---|---|
|  | C % | H % | N % | Cl % |
| Theory | 61.93 | 5.20 | 6.88 | 17.41 |
| Found | 61.69 | 5.14 | 6.95 | 17.45 |

EXAMPLE 18

(RS)-6-Fluoro-3-{1-(2,3,6,7-tetrahydrobenzo[1,2-b:4,5-b'1]difuran-2-ylmethyl)-4-piperidyl[-1,2-benzisoxazole

Stage A 6,7-Dihydrobenzo[1,2-b:4,5-b'[difuran-2-carboxylic acid 30.9 g of 2,3-dihydro-6-formyl-5-hydroxybenzofuran (prepared according to the process described in J. Med. Chem. (1989) 32 p. 1006), 32.8 ml of diethyl bromomalonate and 25.35 g of potassium carbonate are mixed at room temperature in 115 ml of methyl ethyl ketone. The mixture is brought to reflux for 5 hours. It is allowed to cool and the solid is filtered off and rinsed with 200 ml of methyl ethyl ketone. The solvent is evaporated off, the residue is taken up with 500 ml of dichloromethane and the organic phase is washed with 200 ml of saturated aqueous sodium chloride solution and dried over magnesium sulfate. After filtration and evaporation, the product obtained is redissolved in 40 ml of ethanol. A hot solution of 21.9 g of potassium hydroxide dissolved in 220 ml of ethanol is added. The mixture is stirred at room temperature and the solid is filtered off and redissolved in a minimum amount of water. The solution is acidified with 100 ml of 6N hydrochloric acid and kept stirring overnight.

The ethanol is evaporated off and the precipitate formed is filtered off. The product is recrystallized in methanol.

Yield: 53%

Proton nuclear magnetic resonance spectrum (solvent DMSO-$d_6$)

3.3 ppm, t, 2H; 4.6 ppm, t, 2H; 7.0 ppm, s, 1H; 7.6 and 7.5 ppm, s+s, 2H; 13.5 ppm, 1H exchangeable.

Stage B 2,3,6,7-Tetrahydrobenzo[1,2-b:4,5-b']difuran-2-carboxylic acid 11.1 g of sodium are dissolved in 160 ml of toluene using a Bunsen burner. 540 g of mercury are then introduced dropwise. The mixture is left standing for 2 hours at room temperature and then the toluene and, under a stream of nitrogen, the amalgam obtained are allowed to settle. 20 g of the acid obtained in stage A, dissolved in 460 ml of 0.3 N sodium hydroxide, are run onto this amalgam.

The mixture is kept stirring overnight at room temperature, the mercury is separated after settling has taken place and the aqueous phase is acidified in the cold state with 45 ml of concentrated hydrochloric acid. The aqueous phase is filtered and then extracted three times with 500 ml of ethyl acetate. The combined organic phases are washed with 200 ml of a saturated aqueous sodium chloride solution and dried over magnesium sulfate. After filtration and evaporation, the expected acid is recovered.

Yield: 54%

Melting point: 185° C.

Proton nuclear magnetic resonance spectrum (solvent $CDCl_3$):

3.1 ppm, t, 2H; 3.2-3.6 ppm, 2H; 4.5 ppm, 2H; 5.15 ppm, dd, 1H; 6.55 and 6.7 ppm, s+s, 2H.

Stage C 2,3,6,7-Tetrahydrobenzo[1,2-b:4.5-b'[difuran-2-ylmethanol

This compound was prepared according to the process described in Example 2, stage A, from the acid obtained above.

Yield: 85%

Melting point: 103°-105° C.

Proton nuclear magnetic resonance spectrum (solvent $CDCl_3$):

2.05 ppm, t, 1H exchangeable; 2.8 to 3 ppm, m, 1H; 3 to 3.3 ppm, m+t, 1H+2H; 3.7 ppm, 2H; 4.5 ppm, t, 2H; 4.85 ppm, m, 1H; 6.6 ppm, s+s, 2H.

Stage D 2,3,6,7-Tetrahydrobenzo1,2-b:4,5-b,1difuran-2-ylmethyl para-toluenesulfonate This compound was prepared from the alcohol described in the preceding stage, according to the process described in Example 4, stage B.

Yield: 92%

Melting point: 113° C.

Proton nuclear magnetic resonance spectrum (solvent $CDCl_3$):

2.45 ppm, s, 3H; 2.85 ppm, 1H; 3.1 ppm, t, 2H; 3.2 ppm, 1H; 4.15 ppm, d, 2H; 4.5 ppm, 2H; 4.90 ppm, 1H; 6.50 ppm, s+s, 2H; 7.30 ppm, 2H; 7.75 ppm, d, 2H.

Stage E (RS)-6-Fluoro-3-[1-(2,3,6,7-tetrahydrobenzo[1,2-b:4,5-b,]difuran-2-ylmethyl)-4-piperidyl]-1,2-benzisoxazole was obtained according to the process described in Example 13, stage I, but using 2,3,6,7-tetrahydrobenzo[1,2-b:4,5-b']difuran-2-ylmethyl para-toluenesulfonate instead of 2,3-methylenedioxybenzocyclobuten-1-ylmethyl para-toluenesulfonate.

Yield: 20%

Melting point: 117°-121° C.

|  | Elemental analysis | | |
|---|---|---|---|
|  | C % | H % | N % |
| Theory | 70.04 | 5.88 | 7.10 |
| Found | 70.08 | 6.10 | 7.15 |

EXAMPLE 19

(RS)-6-Fluoro-3-[1-indanylanylmethyl)-4-piperidyl]-1,2-benzisoxazole fumarate

Stage A

6-Fluoro-3-[1-(1-indanylcarbonyl-4-piperidyl]-1,2-benzisoxazole 4.2 g of carbonyldiimidazole are added to 3.7 g of 1-indanecarboxylic acid (Synthesis (1987) 845) dissolved in 15 ml of dichloromethane. After stirring for 1 hour 30 minutes at room temperature, 5 g of 6-fluoro-3-piperid-1,2-benzisoxazole, dissolved in 10 ml of dichloromethane, are added. The mixture is stirred for 48 hours at room temperature and then concentrated to dryness and the residue is extracted with ethyl acetate. The organic phase is washed with hydrochloric acid, then with sodium bicarbonate solution and finally with water. It is dried over magnesium sulfate and concentrated. The oil obtained is used without further treatment.

Proton nuclear magnetic resonance spectrum (solvent CDCl₃):

2.15 ppm, m, 2H; 2.25 ppm, m, 2H; 2.45 ppm, m, 2H; 2.9to 3.2 ppm, m+t, 3H; 3.3 to 3.6 ppm, m, 2H; 4.2 to 4.5 ppm, t+m, 2H; 4.75 ppm, t, 1H; 7 to 7.4 ppm, m+m+t, 6H; 7.7 ppm, d, 1H.

Stage B 8 g of the compound described in stage A, in 120 ml of tetrahydrofuran, are introduced in the course of 15 minutes into a suspension, maintained at 0° C., of 1.7 g of lithium aluminum hydride in 60 ml of tetrahydrofuran, taking care that the temperature does not exceed 5° C. The temperature of the reaction medium is allowed to rise to 20° C. After the introduction is complete, the mixture is hydrolyzed for 40 minutes with 1.15 ml of water, 0.92 ml of 20% strength sodium hydroxide and 4.2 ml of water. The mixture is filtered and concentrated.

The oil obtained is purified on a silica column using a mixture of dichloromethane and ethyl acetate (95 : 5 V/V) as eluent.

Yield: 62%

(RS)-6-Fluoro-3-[1-(1-indanyl-methyl)-4-piperidyl]-1,2-benzisoxazole fumarate is obtained by salification of the base with a 2% strength ethanolic solution of fumaric acid.

Melting point: 192°-196° C.

|  | Elemental analysis | | |
|---|---|---|---|
|  | C % | H % | N % |
| Theory | 66.94 | 5.83 | 6.00 |
| Found | 66.97 | 5.91 | 5.90 |

EXAMPLE 20

(RS)-3-[1-(4.5dimethoxybenzocyclobuten-1-ylmethyl -4-piperidyl)-1,2-benzisoxazole hydrochloride

Stage A

3-[1-(4,5-Dimethoxybenzocyclobuten-1-ylcarbonyl)-4-piperidyl]-6-fluoro-1,2-benzisoxazole 8.0 g of 4,5-dimethoxybenzocyclobutene-1-carboxylic acid (prepared according to the process described in Tetrahedron (1973) 29 p. 73) are dissolved in 130 ml of tetrahydrofuran, and 6.9 g of carbonyldiimidazole are added. The mixture is stirred at room temperature for 2 hours until the gaseous evolution has ceased. A solution of 8.5 g of 6-fluoro-3-piperid-4-yl-1,2-benzisoxazole in 100 ml of tetrahydrofuran is then added dropwise. The mixture is stirred at room temperature overnight. The expected product precipitates. It is filtered off and dried in a desiccator over phosphorus pentoxide.

Yield: 63%

Melting point: 178° C.

Proton nuclear magnetic resonance spectrum (solvent CDCl₃):

1.8 to 2.3 ppm, m, 4H; 2.95 ppm, m, 1H; 3.2 to 3.5 ppm, 3m, 4H; 3.85 ppm, s, 6H; 4.15 ppm, m, 1H; 4.4 ppm, t, 1H; 4.65 ppm, m, 1H; 6.65 and 6.80 ppm, 2s, 2H; 7.05 ppm, td, 1H; 7.3 ppm, dd, 1H; 7.65 ppm, dd, 1H.

Stage B (RS)-3-[1-(4,5-Dimethoxybenzocyclobuten-1-ylmethyl)-4-piperidyl]-1,2-benzisoxazole hydrochloride was obtained from the product described above according to the method described in Example 19, stage B.

For the purification of the base, a mixture of dichloromethane and methanol (95 : 5 V/V) was used as elution solvent.

Yield: 52%

The base was salified with a solution of hydrochloric acid in ethyl ether.

Melting point: 259°-268° C.

|  | Elemental analysis: | | | |
|---|---|---|---|---|
|  | C % | H % | N % | Cl % |
| Theory | 63.81 | 6.05 | 6.47 | 8.19 |
| Found | 64.02 | 6.02 | 6.46 | 8.26 |

EXAMPLE 21

(RS)-3-[1-(4-Ethyl-5-methoxybenzocyclobuten-1-ylmethyl)-4-piperidyl]-6-fluoro-1,2-benzisoxazole

Stage A

2-Cyano-3-(2,3-dihydro-5-benzofuranyl)acrylic acid 39.5 g of 2,3-dihydro-5-benzofurancarbaldehyde (prepared according to the process described in J. Org. Chem. (1984), 49, p. 409), 22.7 g of 2-cyanoacetic acid and 4.08 g of ammonium acetate are mixed in 37 ml of pyridine and 210 ml of benzene The mixture is brought to reflux for 6 hours 30 minutes. The precipitate formed is isolated and then suspended in 600 ml of 6 N hydrochloric acid. The solid isolated is filtered off and washed with water and dried in the air.

Yield: 48%

Melting point: 234° C.

Proton nuclear magnetic resonance spectrum (solvent CDCl₃+DMSO-d₆):

3.3 ppm, t, 2H; 4.7 ppm, t, 2H; 6.9 ppm, d, 1H; 7.7 ppm, dd, 1H; 8.05 ppm, s, 1H; 8.15 ppm, s, 1H.

Stage B

2-Cyano-3-(2,3-dihydro-5-benzofuranyl)propionic acid

This product was prepared from the compound obtained in stage A according to the process described in Example 13, stage B.

Yield: 89%

Proton nuclear magnetic resonance spectrum (solvent CDCl₃):

3.0-3.3 ppm, 4H; 3.6 ppm, 1H; 4.55 ppm, t, 2H; 6.75 ppm, d, 1H; 7.0 ppm, 1H; 7.15 ppm, s, 1H; 8.0 ppm, 1H exchangeable

Stage C 5-(2-Cyanoethyl)-2,3-dihydrobenzofuran

This compound was obtained from the acid described in stage B according to the process described in Example 13, stage C.

Yield: 76%

Melting point: 64° C.

Proton nuclear magnetic resonance spectrum (solvent CDCl₃): 2.85 ppm, 2H; 3.2 ppm, 2H; 4.55 ppm, t, 2H; 6.7 ppm, d, 1H; 6.9 ppm, d, 1H; 7.1 ppm, s, 1H.

Stage D

7-Bromo-5-(2-cyanoethyl)-2,3-dihydrobenzofuran

This compound was obtained according to the process described in Example 13, stage D, from 5-(2-cyanoethyl)-2,3-dihydrobenzofuran.

Yield: 96%
Melting point: 73°-74° C.
Proton nuclear magnetic resonance spectrum (solvent CDCl$_3$): 2.6 ppm, t, 2H; 2.9 ppm, t, 2H; 3.25 ppm, t, 2H; 4.6 ppm, t, 2H; 7.0 ppm, s, 1H; 7.1 ppm, s, 1H.

Stage E

2-Bromo-4-(2-cyanoethyl)-6-ethylenylphenol 300 mg of potassium ferricyanide and a few crystals of ferric nitrate are added to 600 ml of ammonia and the mixture is stirred for 15 minutes. 9.2 g of sodium in lumps are dissolved in the course of 30-40 minutes. The mixture is stirred for approximately 1 hour and 25 g of the product obtained in stage D are then added portionwise in the course of approximately 20 minutes. The mixture is kept stirring for 3 hours and 32 g of ammonium nitrate are then added. Stirring is stopped and the ammonia is allowed to evaporate.

Under a nitrogen atmosphere, a few ml of methanol are added, followed by 1.5 liters of water. The aqueous phase is extracted four times with 500 ml of dichloromethane. The combined organic phases are washed with 500 ml of 1N hydrochloric acid and 500 ml of water and then dried over magnesium sulfate. The crude product obtained after filtration and evaporation is recrystallized in 185 ml of ethanol.
Yield: 56%
Melting point: 128° C.
Proton nuclear magnetic resonance scectrum (solvent CDCl$_3$):
2.55 ppm, t, 2H; 2.85 ppm, 2H; 5.65 ppm, 1H exchangeable; 5.35 ppm, dd, 1H; 5.75 ppm, dd, 1H; 6.8 to 7.1 ppm, dd, 1H; 7.2 ppm, 2s, 2H.

Stage F 1-(3-Bromo-4-methoxy-5-ethylenylphenyl)-2-cyanoethane 5.05 ml of dimethyl sulfate are added dropwise in the course of 15 minutes with very vigorous stirring at 8°-10° C. to 13.4 g of the phenol obtained in stage E dissolved in potassium hydroxide The mixture is kept stirring for 19 hours at room temperature and extracted with 3 times 100 ml of ethyl acetate. The combined organic phases are washed twice with 50 ml of 1 N sodium hydroxide and then with 50 ml of water and dried over magnesium sulfate. After filtration and evaporation, the expected product is obtained in the form of an oil.
Yield: 85%
Proton nuclear magnetic resonance spectrum (solvent CDCl$_3$);
2.6 ppm, t, 2H; 2.9 ppm, t, 2H; 3.8 ppm, s, 3H; 5.4 ppm, d, 1H; 5.8 ppm, d, 1H; 7.0 ppm, dd, 1H; 7.35 ppm, m, 2H.

Stage G 1-(3-Bromo-4-methoxy-5-ethylphenyl)-2-cyanoethane

The compound obtained in stage F is hydrogenated at room temperature and at atmospheric pressure for 5 hours in the presence of 220 mg of platinum oxide. The catalyst is filtered off and rinsed with a little acetonitrile. After evaporation, the expected product is obtained in the form of an oil.
Yield: 95%
Proton nuclear magnetic resonance spectrum (solvent CDCl$_3$):
1.2 ppm, t, 3H; 2.5 to 2.8 ppm, c+t, 2H+2H; 2.9 ppm, t, 2H; 3.75 ppm, s, 3H; 7.0 ppm, d, 1H; 7.25 ppm, d, 1H.

Stage H

3-[1-(4-Ethyl-5-methoxybenzocyclobuten-1-ylcarbonyl)-4piperidyl]-6-fluoro-1,2-benzisoxazole This compound was prepared from 6-fluoro-3-piperid- 4-yl-1,2-benzisoxazole and 4-ethyl-5-methoxybenzocyclobuten-1-carboxylic acid according to the process described in Example 20, stage A.

4-Ethyl-5-methoxybenzocyclobutene-1-carboxylic acid was prepared from the compound described in stage G and according to the process described in Example 13, stages E and F.
Yield: 95%
Proton nuclear magnetic resonance spectrum (solvent CDCl$_3$):
1.15 ppm, t, 3H; 1.8 to 2.3 ppm, m, 4H; 2.6 ppm, q, 2H; 3.0 ppm, 1H; 3.3 to 3.5 ppm, m+m+m, 2H+1H+1H; 3.75 ppm, s, 3H; 4.15 ppm, m, 1H; 4.4 ppm, 1H; 4.65 ppm, 1H; 6.7 ppm, s, 1H; 6.85 ppm, 1H; 7.05 ppm, td, 1H; 7.25 ppm, dd, 1H; 7.6 ppm, dd, 1H.

Stage I (RS)-3-[1 TM (4-Ethyl-5-methoxybenzocyclobuten-1-ylmethyl)-4-piperidyl]-6-fluoro-1,2-benzisoxazole was obtained according to the process described in Example 19, stage B, from the compound described above.
Yield: 24%
Melting point: 92°-97° C.

|  | Elemental analysis | | |
|---|---|---|---|
|  | C % | H % | N % |
| Theory | 73.07 | 6.90 | 7.10 |
| Found | 72.62 | 7.02 | 7.01 |

EXAMPLE 22

(RS)-3-[1-(3-Benzocyclobuten-1-ylpropyl)-4-piperidyl]-6-fluoro-1,2-benzisoxazole fumarate

Stage A

Diethyl 2-(benzocyclobuten-1-ylmethyl)malonate

Sodium ethylate is prepared by dissolving 0.07 mole of sodium in 35.5 ml of ethanol. 0.073 mole of diethyl malonate is then introduced. The mixture is left stirring for 1 hour at room temperature and 0.069 mole of benzocyclobuten-1-ylmethyl para-toluenesulfonate is then added. The mixture is left for 1 hour and then heated to reflux for 14 hours. It is concentrated, the residue is taken up with dichloromethane and the organic phase is washed several times with water. The product is purified on a silica column using a mixture of cyclohexane and dichloromethane (95 : 5 V/V) as eluent.
Yield: 55%
Proton nuclear magnetic resonance spectrum (solvent CDCl$_3$):
1.2 to 1.45 ppm, m, 6H; 2.2 to 2.4 ppm, m, 2H; 2.75 ppm, 2d, 1H; 3.3 to 3.6 ppm, m, 3H; 4.1 to 4.3 ppm, m, 4H; 7.0 to 7.2 ppm, m, 4H.

Stage B 2-(Benzocyclobuten-1-ylmethyl)malonic acid 0.16 mole of potassium hydroxide is dissolved in 10 ml of water. The solution is heated to 100° C. and the diester described above (0.041 mole) is then introduced in the course of 1 hour while the alcohol formed is distilled off. Heating is continued for 3 hours. The aqueous phase is washed several times with ethyl ether. It is acidified with concentrated hydrochloric acid. The product is extracted with dichloromethane and dried.
Yield: 67%
Melting point: 164°-167° C.

Stage C

3-Benzocyclobuten-1-ylpropionic acid 0.027 mole of the diacid obtained in stage B is mixed in 20 ml of N,N-dimethylacetamide and the mixture is heated to 125° C. for 5 hours. It is taken up with water and extracted with ethyl ether. The ether phase is washed repeatedly several times with water and concentrated
Yield: 75%
Melting point: <50° C.

Stage D

3-[1-(3-Benzocyclobuten-1-ylpropyl)-4-piperidyl]-6-fluoro-1,2-benzisoxazole was obtained according to the process described in Example 19 (stages A and B), using as the acid the compound described in stage C above.
Yield: 11%
The fumarate was recrystallized in ethanol.
Melting point: 171°-174° C.

|  | Elemental analysis: | | |
|---|---|---|---|
|  | C % | H % | N % |
| Theory | 67.49 | 6.08 | 5.83 |
| Found | 67.00 | 6.10 | 5.59 |

EXAMPLE 23

6-Fluoro-3-[1-(2-indanylmethyl)-4-piperidyl]-1,2-benzisoxazole fumarate

This compound was prepared from 2-indanecarboxylic acid and 6-fluoro-3-piperid-4-yl-1,2-benzisoxazole according to the process described in Example 19, stages A and B.
Yield: 13%
The salt was obtained after the addition of a suitable quantity of fumaric acid dissolved in ethanol.
Melting point: 211°-216° C.

|  | Elemental analysis: | | |
|---|---|---|---|
|  | C % | H % | N % |
| Theory | 66.94 | 5.83 | 6.00 |
| Found | 66.72 | 5.84 | 5.91 |

EXAMPLE 24

(RS)-3-[1-(3-Fluorobenzocyclobuten-1-ylmethyl)-4-piperidyl)-6-fluoro-1,2-benzisoxazole This compound was obtained according to the process described in Example 19, stages A and B, but using 3-fluorobenzocyclobutene-1-carboxylic acid instead of 1-indanecarboxylic acid.

3-Fluorobenzocyclobutene-1-carboxylic acid was prepared from 3-fluorobenzaldehyde according to the process described in Example 13, stages A-F.
Yield: 63% (final stage)
Melting point: 81°-83° C.

|  | Elemental analysis: | | |
|---|---|---|---|
|  | C % | H % | N % |
| Theory | 71.17 | 5.69 | 7.90 |
| Found | 71.16 | 5.80 | 7.73 |

EXAMPLE 25

(RS)-6-Fluoro-3-(1-(5-methoxybenzocyclobuten-1-ylmethyl)-4-piperidyl]-1,2-benzisoxazole This compound was obtained according to the process described in Example 19, stages A and B. The acid used for its preparation is 5-methoxybenzocyclobutene-1-carboxylic acid.

The latter compound was synthesized according to the procedure described in Tetrahedron (1974) 30 p. 1053 and in Example 13, stage F.
Yield: 33% (final stage)
Melting point: 115°-116° C.

|  | Elemental analysis: | | |
|---|---|---|---|
|  | C % | H % | N % |
| Theory | 72.11 | 6.33 | 7.64 |
| Found | 71.89 | 6.40 | 7.66 |

EXAMPLE 26

(RS)-6-Fluoro-3-[1-(4-methoxybenzocyclobuten-1-ylmethyl)-4-piperidyl]-2-benzisoxazole This compound was obtained according to the process described in Example 19, stages A and B, using 4-methoxybenzocyclobutene-1-carboxylic acid in stage A as the acid.

The latter compound was prepared from 1-cyano-4-methoxybenzocyclobutene (J. Am. Chem. Soc (1976), 98 (11), p. 3378) according to the process described in Example 13, stage F.
Yield: 22% (final stage)
Melting point: 97°-99° C.

|  | Elemental analysis: | | |
|---|---|---|---|
|  | C % | H % | N % |
| Theory | 72.11 | 6.33 | 7.64 |
| Found | 71.85 | 6.34 | 7.56 |

EXAMPLE 27

(RS)-3-[1-(Benzocyclobuten-1-ylmethyl)-4-piperidyl]-1,2-benzisoxazole hydrochloride

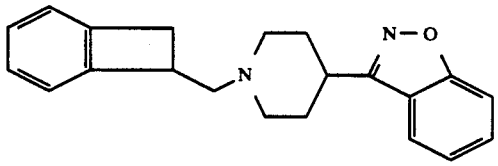

Stage A

2-Fluorobenzoyl-1-methylpiperidine

The magnesium compounds is prepared from 0.067 mole of 4-chloro-1-methylpiperidine and 0.055 gram-atom of magnesium in tetrahydrofuran. The reaction is initiated with a few drops of bromoethane.

0.07 mole of 2-fluorobenzonitrile is then introduced into the magnesium compounds. The mixture is brought to reflux for 2 hours and then left overnight at room temperature. It is hydrolyzed with a solution of 5.3 g of ammonium chloride, 45 g of ice and 50 ml of water. The mixture is brought to reflux for 3 hours. It is allowed to cool. It is extracted several times with ethyl ether. The oil obtained is dried.

Yield: 50%

Proton nuclear magnetic resonance spectrum (solvent CDCl$_3$):

1.7-2.15 ppm, m, 6H; 2.25 ppm, s, 3H; 2.85 ppm, , 2H; 3.1 ppm, m, 1H; 7.0-7.3 ppm, m, 4H.

Stage B

1-Ethoxycarbonyl-4-(2-fluorobenzoyl)piperidine 37 ml of ethyl chloroformate are added dropwise to a solution of 0.19 mole of the compound obtained in the preceding stage dissolved in 340 ml of toluene. The mixture is heated to 85° C. for 8 hours and 10 ml of ethyl chloroformate are then added. Heating is resumed for 4 hours. The reaction mixture is washed with water and then with hydrochloric acid.

Yield: 54%

Proton nuclear magnetic resonance spectrum (solvent CDCl$_3$):

1.05-1.15 ppm, m, 4H; 1.25 ppm, t, 3H; 2.95 ppm, m, 2H; 3.3 ppm, m, 1H; 3.4 ppm, m, 1H; 3.75 ppm, m, 1H; 4.15 ppm, q, 2H; 7.05-7.3 ppm, m, 2H; 7.55 ppm, m, 1H; 7.8 ppm, dd, 1H.

Stage C

3-Piperid-4-yl-1,2-benzisoxazole

This product was obtained from a compound described in stage B according to the process described in Example 1, stages D-F.

Yield: 30%

Proton nuclear magnetic resonance spectrum (solvent CDCl$_3$):

1.7 ppm, 1H exchangeable; 1.8-2.2 ppm, m, 4H; 2.85 ppm, td, 2H; 3.15-3.4 ppm, m, 3H; 7.25 ppm, td, 1H; 7.5 ppm, m, 2H; 7.75 ppm, d, 1H.

Stage D

3-[1-(Benzocyclobuten-1-ylmethyl)-4-piperidyl]-1,2-benzisoxazole was prepared from benzocyclobutene-1-carboxylic acid and 3-piperid-4-yl-1,2-benzisoxazole according to the process described in Example 19, stages A and B.

The hydrochloride was obtained after salification with ethereal hydrogen chloride.

Yield: 23%

Melting point: 208°-212° C.

| | Elemental analysis: | | | |
|---|---|---|---|---|
| | C % | H % | N % | Cl % |
| Theory | 71.08 | 6.53 | 7.89 | 9.99 |
| Found | 70.70 | 6.51 | 7.72 | 10.28 |

Proton nuclear magnetic resonance spectrum (solvent DMSO-d$_6$): 2.1-2.5 ppm, m, 4H; 3-3.85 ppm, m, 9H; 4.05 ppm, m, 1H; 7.1-7.3 ppm, m, 4H; 7.45 ppm, td, 1H; 7.7 ppm, td, 1H; 7.75 ppm, d, 1H; 8.2 ppm, d, 1H; 11-11.4 ppm, m exchangeable, 1H.

EXAMPLE 28

(−)-3-[1-(Benzocyclobuten-1-ylmethyl)-4-piperidyl]-6-fluoro-1,2-benzisoxazole The compound of Example 1 is dissolved in water alkalinized with sodium hydroxide. The aqueous solution is extracted with ether. After settling has taken place, the organic phase is dried over anhydrous magnesium sulfate and evaporated to dryness to obtain (RS)-3-[1-(benzocyclobuten-1-ylmethyl)-4-piperidyl]-6-fluoro-1,2benzisoxazole.

6.54 g of (+)-camphorsulfonic acid, dissolved in 327 ml of ethanol, are added to 8.8 g of (RS)-3-[1-(benzocyclobuten- 1-ylmethyl)-4-piperidyl]-6-fluoro-1,2-benzisoxazole. The solution is left overnight at room temperature and the precipitate formed is then isolated. The product is recrystallized in 230 ml of ethanol, alkalinized with sodium hydroxide and extracted with ether. The organic phase is dried over anhydrous magnesium sulfate and evaporated to dryness to obtain (−)-3-[1-(benzocyclobuten-1-ylmethyl)-4-piperidyl]-6-fluoro-1,2-benzisoxazole.

Melting point: 78°-82° C.

Proton nuclear magnetic resonance spectrum (solvent CDCl$_3$):

2 to 2.4 ppm, m+m, 4H+2H; 2.65 ppm, dd, 1H; 2.75 ppm, m, 2H; 3 to 3.2 ppm, m+m, 1H+2H; 3.4 ppm, dd, 1H; 3.7 ppm, 1H; 6.9 to 7.3 ppm, m, 6H; 7.7 ppm, dd, 1H.

| Optical rotation (C = 1% in CHCl$_3$): | |
|---|---|
| λ nm | [α]$_D^{20°}$ C. |
| 589 | −9.1° |
| 578 | −9.45° |
| 546 | −10.75° |
| 436 | −18.8° |

EXAMPLE 29

(−)-3-[1-(Benzocyclobuten-1-ylmethyl)-4-piperidyl]-6-fluoro-1,2-benzisoxazole fumarate 45 ml of a 0.072M solution of fumaric acid in ethanol are added to 2.5 g of optically active base obtained in Example 28. The mixture is left to precipitate overnight to obtain (−)-3-[1-(benzocyclobuten-1-ylmethyl)-4-piperidyl]-6-fluoro-1,2-benzisoxazole fumarate Melting point: 156°-160° C.

Proton nuclear magnetic resonance spectrum (solvent CDCl$_3$):

1.9 to 2.1 ppm, m, 4H; 2.6 ppm, m, 2H; 2.7 to 3.0 ppm, m, 3H; 3.1 to 3.5 ppm, m, 4H; 3.8 ppm, m, 1H; 6.6 ppm, s, 2H; 7.0 to 7.2 ppm, m, 4H; 7.3 ppm, m, 1H; 7.7 ppm, dd, 1H; 8.05 ppm, dd, 1H.

| Optical rotation (C = 1% in DMSO): | |
|---|---|
| λ nm | [α]$_D^{25°}$ C. |
| 589 | −5.85° |
| 578 | −6.40° |
| 546 | −7.35° |
| 436 | −12.1° |

EXAMPLE 30

(+)-3-[1-(Benzocyclobuten-1-ylmethyl-4-piperidyl]-6-fluoro-1.2-benzisoxazole

This compound was obtained according to the process described in Example 28, but using (−)-camphorsulfonic acid.

Melting point: oil

| Optical rotation (C = 1% in CHCl₃): | |
|---|---|
| λ nm | $[\alpha]_D^{22°\ C.}$ |
| 589 | +9.35° |
| 578 | +9.85° |
| 546 | +11.40° |
| 436 | +20.95° |

EXAMPLE 31

(+)-3-[1-(Benzocyclobuten-1-ylmethyl)-4-piperidyl]-6-fluoro-1,2-benzisoxazole fumarate This compound was prepared from (+)-3-[1-(benzocyclobuten-1-ylmethyl)-4-piperidyl]-6-fluoro TM 1,2-benzisoxazole according to the process described in Example 29.

| Optical rotation (C = 1% in DMSO): | |
|---|---|
| λ nm | $[\alpha]_D^{25°\ C.}$ |
| 589 | +6.1° |
| 578 | +6.4° |
| 546 | +7.25° |
| 436 | +12.7° |

EXAMPLE 32

(RS)-6-Fluoro-3-[1-(4,5-methylenedioxybenzocyclobuten-1-ylmethyl)-4-piperidyl]-1,2-benzisoxazole

Stage A

6-Fluoro-3-[1-(4,5-methylenedioxybenzocyclobuten-1-ylcarbonyl)-4-piperidyl]-1,2-benzisoxazole This compound was prepared according to the process described in Example 19, stage A, but using 4,5-methylenedioxybenzocyclobutene-1-carboxylic acid as the acid. The latter product was obtained from 3,4-methylenedioxybenzaldehyde using the protocol described in Example 13, stages A-F.

Yield: 30%

Melting point: 228°-230° C.

Proton nuclear magnetic resonance spectrum (solvent CDCl₃):

1.8-2.3 ppm, m, 4H; 3 ppm, t, 1H; 3.2 to 3.5 ppm, 3m, 4H; 4.2 ppm, d, 1H; 4.35 ppm, d, 1H; 4.65 ppm, d, 1H; 5.9 ppm, 2s, 2H; 6.65 and 6.75 ppm, 2s, 2H; 7.1 ppm, td, 1H; 7.25 ppm, dd, 1H; 7.65 ppm, dd, 1H.

Stage B

From the compound described above, using the protocol described in Example 19, stage B, (RS)-6-fluoro-3-[1-(4,5-methylenedioxybenzocyclobuten-1-ylmethyl)-4-piperidyl]-1,2-benzisoxazole is obtained.

Melting point: 125°-126° C.

EXAMPLE 33

(RS)-6-Fluoro-3-[1-(4,5-ethylenedioxybenzocyclobuten-1-ylmethyl)-4-piperidyl]-1,2-benzisoxazole

Stage A

3-[1-(4,5-Ethylenedioxybenzocyclobuten-1-ylcarbonyl)-4-piperidyl]-6-fluoro-1,2-benzisoxazole This compound was prepared according to the process described in Example 32, stage A. The acid used is 4,5-ethylenedioxybenzocyclobutene-1-carboxylic acid.

Yield: 48%

Proton nuclear magnetic resonance spectrum (solvent CDCl₃):

1.8 to 2.3 ppm, m, 4H; 3 ppm, t, 1H; 3.2 to 3.6 ppm, 3m, 4H; 4.15 ppm, m, 1H; 4.2 ppm, 4H; 4.4 ppm, d, 1H; 4.65 ppm, d, H; 6.6 ppm, s, 1H; 6.7 ppm, s, 1H; 7.05 ppm td, 1H; 7.25 ppm, m, 1H; 7.65 ppm, dd, 1H.

Stage B

From the compound described above, using the protocol described in Example 19, stage B, (RS)-6-fluoro-3-[1-(4,5-ethylenedioxybenzocyclobuten-1-ylmethyl)-4-piperidyl]-1,2-benzisoxazole is obtained

EXAMPLE 34

(RS)-6-Fluoro-3-1-(4,5,6-trimethoxybenzocyclobuten-1-ylcarbonyl)-4-piperidyl]-1,2-benzisoxazole

Stage A

6-Fluoro-3-[1-(4,5,6-trimethoxybenzocyclobuten-1-ylcarbonyl)-4-piperidyl]-1,2-benzisoxazole This compound was prepared using the protocol described in Example 32, stage A. The acid used is 4,5,6-trimethoxybenzocyclobuten-1-carboxylic acid.

Yield: 26%

Proton nuclear magnetic resonance spectrum (solvent CDCl₃):

2.3 to 1.8 ppm, m, 4H; 3 ppm, m, 1H; 3.2 to 4 ppm, m+m+m, 4H; 3.9-3.8-3,65 ppm, 3s, 9H; 4.15 ppm, m, 1H; 4.4 ppm, m, 1H; 4.6 ppm, m, 1H; 6.5 ppm, s, 1H; 7.1 ppm, m, 1H; 7.65 ppm, m, 1H; 7.75 ppm, m, 1H.

Stage B (RS)-6-Fluoro-3-[1-(4,5,6-trimethoxybenzocyclobuten- 1-ylmethyl)-4-piperidyl]-1,2-benzisoxazole is obtained from the compound described above using the process described in Example 19, stage B..

Melting point: 141°-143° C.

TABLE I

| EX. | R | m | n | p | NMR (Solvent) |
|---|---|---|---|---|---|
| 1 | benzocyclobutenyl-CH | 1 | 2 | 0 | (CD$_3$OD) (hydriodide) 2.1 to 2.6 ppm, m, 4H; 3.0 to 4.0 ppm, m, 9H; 4 ppm, m, 1H 7.0 to 7.35 ppm, m, 5H; 7.4 ppm, dd, 1H; 8 ppm, m, 1H. |
| 2 | benzocyclobutenyl-CH | 2 | 2 | 0 | (DMSO-d$_6$) (fumarate) 1.2 to 1.7 ppm, m, 6H; 2.2 to 2.8 ppm, m+m+m, 1H+2H+2H; 3.0 to 3.5 ppm, m, 4H+2H exchangeable; 3.4 ppm, m, 1H; 6.55 ppm, d, 2H; 7.0 to 7.3 ppm, m, 4H; 7.2 ppm, t, 1H; 7.7 ppm, dd, 1H; 8.05 ppm, dd, 1H. |
| 3 | benzocyclobutenyl-C(CH$_3$) | 1 | 2 | 0 | (CDCl$_3$) (fumarate) 1.85 ppm, s, 3H; 2.0 to 2.3 ppm, m, 4H; 2.7 to 4.0 ppm, m, 9H; 7.0 to 7.3 ppm, m, 5H; 7.6 ppm, m, 1H; 8.55 ppm, m, 1H; 12.1 ppm, 1H exchangeable; 12.7 ppm, 1H exchangeable |
| 4 | 2,3-dihydrobenzofuranyl | 1 | 2 | 0 | (CDCl$_3$) (base) 2.1 ppm, m, 4H; 2.4 ppm, m, 2H; 2.6 to 3.5 ppm, m, 7H; 5.1 ppm, m, 1H; 6.4 to 7.3 ppm, m, 4H+2H; 7.75 ppm, dd, 1H |
| 5 | 7-methoxy-2,3-dihydrobenzofuranyl | 1 | 2 | 0 | (CDCl$_3$) (base) 1.95 to 2.25 ppm, m, 4H; 2.4 ppm, m, 2H; 2.7 ppm, dd, 1H; 2.9 ppm, dd, 1H; 2.95 to 3.25 ppm, m, 4H; 3.35 ppm, dd, 1H; 3.9 ppm, s, 3H; 5.05 ppm, m, 1H; 6.7 to 6.85 ppm, m, 3H; 7.05 ppm, td, 1H; 7.2 ppm, dd, 1H; 7.7 ppm, dd, 1H |
| 6 | 5-fluoro-2,3-dihydrobenzofuranyl | 1 | 2 | 0 | (CDCl$_3$) (base) 2.0 to 2.5 ppm, m, 6H; 2.6 to 3.4 ppm, m, 7H; 5.0 ppm, m, 1H; 6.6 to 6.95 ppm, m, 3H; 7.05 ppm, td, 1H; 7.25 ppm, dd, 1H; 7.5 ppm, dd, 1H |
| 7 | benzofuranyl | 1 | 2 | 0 | (DMSO-d$_6$) (hydrochloride) 2.1 to 2.5 ppm, m, 4H; 3.25 ppm, m, 2H; 3.5 ppm, m, 1H; 3.65 ppm, m, 2H; 4.65 ppm, s, 2H; 7.2 to 7.5 ppm, m, 4H; 7.7 ppm, m, 3H; 8.2 ppm, dd, 1H; 11.7 ppm, 1H exchangeable |
| 8 | chromon-3-yl | 1 | 2 | 0 | (DMSO-d$_6$) (hydrochloride) 2.0 to 2.6 ppm, m, 4H; 3.0 to 3.2 ppm, m, 5H; 4.5 ppm, s, 2H; 6.8 ppm, s, 1H; 7.35 ppm, m, 1H; 7.55 ppm, t, 1H; 7.75 ppm, m, 2H; 7.9 ppm, m, 1H; 8.10 ppm, m, 1H; 8.25 ppm, m, 1H |
| 9 | 1-(3-trifluoromethylphenyl)-1,8-naphthyridin-2(1H)-on-3-yl | 2 | 2 | 0 | (DMSO-d$_6$) (hydrochloride) 2.1 to 2.6 ppm, m, 4H; 3.05 to 3.8 ppm, m, 9H; 7.3 ppm, m, 2H; 7.45 to 7.9 ppm, m, 5H; 8.05 to 8.3 ppm, m, 3H; 8.4 ppm, dd, 1H; 11.05 ppm, 1H exchangeable |

TABLE I-continued

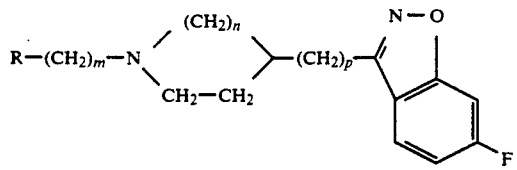

| EX. | R | m | n | p | NMR (Solvent) |
|---|---|---|---|---|---|
| 10 | (chlorobenzocyclobutene with methyl) | 1 | 2 | 0 | (CDCl₃) (base) 2 to 2.4 ppm, m+m, 6H; 2.6 to 2.9 ppm, m+m, 3H; 3.1 ppm, m+m, 3H; 3.3 ppm, dd, 1H; 3.65 ppm, m, 1H; 6.9 to 7.3 ppm, m+m, 5H; 7.7 ppm, dd, 1H |
| 11 | (isopropyl-dihydrobenzofuran with methyl) | 1 | 2 | 0 | (DMSO-d₆) (fumarate) 1.2 ppm, dd, 6H; 1.7 to 2.2 ppm, m, 4H; 2.4 ppm, m, 1H; 2.60 to 2.85 ppm, m, 2H; 2.85 to 3.55 ppm, m, 7H; 5.0 ppm, m, 1H; 6.6 ppm, s, 2H; 6.75 ppm, t, 1H; 6.95 to 7 ppm, 2d, 2H; 7.25 ppm, td, 1H; 7.7 ppm, dd, 1H; 8.0 ppm, dd, 1H |
| 12 | (fluoro-dihydrobenzofuran with methyl) | 1 | 2 | 0 | (CDCl₃) (base) 2 ppm, m, 4H; 2.5 to 2.25 ppm, m, 2H; 3.0 to 2.5 ppm, m, 2H; 3.0 to 3.5 ppm, m, 5H; 5.1 ppm, m, 1H; 6.5 to 7.1 ppm, m, 4H; 7.2 ppm, m, 1H; 7.7 ppm, dd, 1H |
| 13 | (methylenedioxy-benzocyclobutene with methyl) | 1 | 2 | 0 | (DMSO-d₆) (fumarate) 2.1-2.6 ppm. m, 4H; 3-4 ppm, m, 9H; 4 ppm, m, 1H; 6.0 ppm, d, 2H; 6.6 ppm, s, 2H; 6.8 ppm, (syst. AB), 2H; 7.35 ppm, td, 1H; 7.6 ppm, dd, 1H; 8.05 ppm, dd, 1H |
| 14 | (methyl-phenyl-naphthyridinone) | 2 | 2 | 0 | (CDCl₃) (base) 2.05 ppm, m, 4H; 2.25 ppm, m, 2H; 2.7-3.0 ppm, m, 4H; 3.10 ppm, m, 1H; 3.20 ppm, m, 2H; 7.0-7.3 ppm, m, 5H; 7.4-7.75 ppm, m, 5H; 7.9 ppm, dd, 1H; 8.4 ppm, dd, 1H |
| 15 | (methyl-fluorophenyl-naphthyridinone) | 1 | 2 | 0 | (CDCl₃) (base) 2-2.3 ppm, m, 4H; 2.4 ppm, m, 2H; 3.1 ppm, m+m, 1H+2H; 3.65 ppm, s, 2H; 6.9-7.4 ppm, m+m+td, 2H+3H+1H; 7.5 ppm, m, 1H; 7.7 ppm, dd, 1H; 7.9 ppm, s, 1H; 7.9 ppm, dd, 2H; 8.4 ppm, dd, 1H |
| 16 | (indane) | 0 | 2 | 0 | (CDCl₃) (base) 2-2.4 ppm, m, 6H; 2.8 to 3.4 ppm, m, 8H; 6.9 to 7.3 ppm, m+m, 2H+4H; 7.7 ppm, dd, 1H |
| 17 | (chloro-benzocyclobutene with methyl) | 1 | 2 | 0 | (CDCl₃) (hydrochloride) 2.1 to 2.5 ppm, m, 4H; 3.0 to 3.8 ppm, 5m, 9H; 4.05 ppm, m, 1H; 7.1 to 7.4 ppm, 2m, 4H; 7.75 ppm, dd, 1H; 8.25 ppm, dd, 1H; 11.15 ppm, m, 1H exchangeable |

TABLE I-continued

R—(CH$_2$)$_m$—N(CH$_2$)$_n$/CH$_2$—CH$_2$ —CH(CH$_2$)$_p$—C(=N—OH)—(2-hydroxy-4-fluorophenyl)

| EX. | R | m | n | p | NMR (Solvent) |
|---|---|---|---|---|---|
| 18 | (2,3-dihydrobenzofuran-5-yl-methyl, oxygen-containing bicyclic) | 1 | 2 | 0 | (CDCl$_3$) (base) 1.9 to 2.3 ppm, m, 4H; 2.3 ppm, m, 2H; 2.6 ppm, dd, 1H; 2.7 to 3.3 ppm, m+t+dd+m+m, 1H+2H+1H+2H+2H; 4.5 ppm, t, 2H; 4.95 ppm, m, 1H; 6.6 ppm, s+s, 2H; 7.05 ppm, td, 1H; 7.2 ppm, dd, 1H; 7.7 ppm, dd, 1H |
| 19 | (indanyl) | 1 | 2 | 0 | (DMSO-d$_6$) (fumarate) 2.5 to 1.7 ppm, m, 8H; 2.6 ppm, m, 1H; 2.85 ppm, m, 3H; 3.25 ppm, m, 3H; 3.45 ppm, m, 1H; 5 to 9 ppm, s, 1H; 6.6 ppm, s, 2H; 7.1 to 7.4 ppm, m, 5H; 7.7 ppm, d, 1H; 8.05 ppm, d, 1H |
| 20 | (4,5-dimethoxy-benzocyclobutenyl) CH$_3$O—, CH$_3$O— | 1 | 2 | 0 | (DMSO-d$_6$) (fumarate) 2.2 ppm, m, 2H; 2.5 ppm, m, 2H; 2.9 to 3.8 ppm, 4m, 9H; 3.75 ppm, s, 6H; 3.95 ppm, m, 1H; 6.8 and 6.9 ppm, 2s, 2H; 7.35 ppm, td, 1H; 7.75 ppm, dd, 1H; 8.3 ppm, m, 1H; 11.3 ppm, m, 1H exchangeable |
| 21 | (4-ethyl-5-methoxy-benzocyclobutenyl) C$_2$H$_5$—, CH$_3$O— | 1 | 2 | 0 | (CDCl$_3$) (base) 1.15 ppm, t, 3H; 2.0 to 2.4 ppm, m, 2H+4H; 2.53 ppm, q, 2H; 2.6 to 2.9, m, 2H; 2.89 ppm, dd, 1H; 3.0 to 3.25 ppm, m, 1H+2H; 3.34 ppm, dd, 1H; 3.58 to 3.75 ppm, m, 1H; 3.82 ppm, s, 3H; 6.68 ppm, s, 1H; 6.87 ppm, s, 1H; 7.07 ppm, td, 1H; 7.25 ppm, dd, 1H; 7.72 ppm, dd, 1H |
| 22 | (benzocyclobutenyl) | 3 | 2 | 0 | (DMSO-d$_6$) (fumarate) 1.75–2.15 ppm, m, 8H; 2.5–2.85 ppm, m, 5H; 3.3 ppm, m, 4H; 3.5 ppm, m, 1H; 6.6 ppm, s, 2H; 7.15 ppm, m, 4H; 7.3 ppm, td, 1H; 7.7 ppm, dd, 1H; 8.05 ppm, dd, 1H |
| 23 | (indan-2-yl) | 1 | 2 | 0 | (DMSO-d$_6$) (fumarate) 1.75–2.2 ppm, m, 4H; 2.35 ppm, td, 2H; 2.5–2.85 ppm, m, 5H; 2.85–3.3 ppm, m, 5H; 4–7 ppm, 2H exchangeable; 6.55 ppm, s, 2H; 7–7.3 ppm, m, 4H; 7.3 ppm, td, 1H; 7.7 ppm, dd, 1H; 8.05 ppm, dd, 1H |
| 24 | (3-fluoro-benzocyclobutenyl) F— | 1 | 2 | 0 | (CDCl$_3$) (base) 2.0 to 2.4 ppm, m, 6H; 2.6 to 3.2 ppm, m+m+m+m, 6H; 3.4 ppm, m, 1H; 3.7 ppm, m, 1H; 6.7 to 7.3 ppm, m+m, 5H; 7.7 ppm, dd, 1H |
| 25 | (4-methoxy-benzocyclobutenyl) CH$_3$O— | 1 | 2 | 0 | (CDCl$_3$) (base) 2.0 to 2.35 ppm, m, 6H; 2.6 to 2.95 ppm, m, 3H; 3.15 ppm, m, 3H; 3.3 ppm, dd, 1H; 3.65 ppm, m, 1H; 3.8 ppm, s, 3H; 6.75 ppm, d, 1H; 7 ppm, d, 2H; 7.1 ppm, t, 1H; 7.25 ppm, d, 1H; 7.75 ppm, dd, 1H |
| 26 | (5-methoxy-benzocyclobutenyl) CH$_3$O— | 1 | 2 | 0 | (CDCl$_3$-d$_6$) (base) 2.0 to 2.4 ppm, m+m, 6H; 2.6 to 2.9 ppm, dd+m, 3H; 3.1 ppm, m, 1H; 3.15 ppm, d, 2H; 3.3 ppm, dd, 1H; 3.65 ppm, m, 1H; 3.8 ppm, s, 3H; 6.7 ppm, m, 2H; 7 ppm, d, 1H; 7.05 ppm, td, 1H; 7.25 ppm, dd, 1H; 7.7 ppm, dd, 1H |

TABLE I-continued

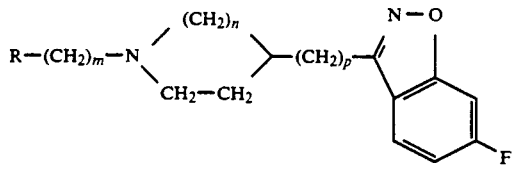

| EX. | R | m | n | p | NMR (Solvent) |
|---|---|---|---|---|---|
| 32 | [benzodioxole group] | 1 | 2 | 0 | (CDCl$_3$-d$_6$) (base) 2.0 to 2.4 ppm, m+m, 2H+4H; 2.5 to 2.8 ppm, m+dd+dd, 1H+1H+1H; 3 to 3.3 ppm, dd+m+d, 1H+1H+2H; 3.5 ppm, m, 1H; 5.85 ppm, s, 2H; 6.65 ppm, 2s, 2H; 7 ppm, td, 1H; 7.2 ppm, dd, 1H; 7.7 ppm, dd, 1H |
| 34 | [trimethoxyphenyl group with CH$_3$O, CH$_3$O, CH$_3$O] | 1 | 2 | 0 | (CDCl$_3$-d$_6$) (base) 2.15 ppm, m, 4H; 2.3 ppm, m, 2H; 2.6 to 3 ppm, m, 2H; 3 to 3.3 ppm, d+m+dd, 2H+1H+1H; 3.6 ppm, dd, 1H; 3.7 ppm, m, 1H; 3.8 to 3.95 ppm, 3s, 9H; 6.4 ppm, s, 1H; 7.1 ppm, td, 1H; 7.25 ppm, dd, 1H; 7.7 ppm, dd, 1H |

PHARMACOLOGICAL STUDY

EXAMPLE 35

Test of methylphenidate-induced stereotypy in rats

For the test, 24 male Wistar rats weighing between 220 and 240 g, fasted for approximately 24 hours, were used. Each animal receives a first treatment (haloperidol, products of the invention or solvent) at a specified time before the second treatment (methylphenidate or physiological saline) performed i.p. at time To. Of the 24 animals used in a test, four serve as a control and receive the following treatments: saline +saline i.p. 1 animal (saline control), solvent and methylphenidate 40 mg/kg i.p. 2 animals (methylphenidate 40 mg/kg i.p. controls) and solvent+methylphenidate 0.16, 0.63, 2.5 or 10 mg/kg i.p. 1 animal (methylphenidate 0.16, 0.63, 2.5 or 10 controls).

The test products were administered to the remaining 20 animals at given times before the i.p. injection at To of 40 mg/kg of methylphenidate. (Observation time for each animal 10 sec.). The behavioral observations took place 30 minutes (T30 min) after the treatment with methylphenidate. A total of 10 observation periods is carried out for each rat at T30 min. During these observations, the presence (1) or absence (0) of stereotypy and the presence of the sign of body flattening are noted. The dose of the test compounds which causes catalepsy is also noted. The statistical analysis consisted in comparing, for a given stereotypic behavior, the score rates (0 to 10) obtained by a group of animals which had received the same treatment with those obtained by the "methylphenidate 40 control" animal group, according to a Mann-Whitney test with the significance at P 0.05 (Siegel S. and Castelan N. J., 1988).

The results of the study demonstrated that the minimum dose of haloperidol, administered i.p., which causes catalepsy is 0.63 mg/kg. The cataleptic dose of the compounds of the invention, evaluated under the same conditions, is very much higher. For example, for the compound of Example 1, the cataleptic dose is >160 mg/kg, and this dose was the maximum dose tested. In effect, the compounds of the invention are only very weakly cataleptogenic, which constitutes a very considerable advantage compared to haloperidol.

The ratios of the cataleptic doses to the doses which inhibit the different parameters studied, after treatment with haloperidol or after treatment with the compounds of the invention and i.p. injection of 40 mg/kg of methylphenidate, are given in Table II.

TABLE II

| COMPOUND | CHEWING | LOCOMOTION | SNIFFING | REARING |
|---|---|---|---|---|
| HALOPERIDOL | 0.63/0.16 = 3.9 | 0.63/0.63 = 1 | 0.63/0.63 = 1 | 0.63/0.63 = 1 |
| EXAMPLE 1 | >160/2.5 = >64 | >160/2.5 = >64 | >160/2.5 = >64 | >160/2.5 = >64 |

The results in this table demonstrate the advantageous activity of the products of the invention compared to haloperidol. The dose of haloperidol necessary for having a total inhibition of all methylphenidate-induced stereotypy in rats is identical to the cataleptic dose (ratio equal to 1). In contrast, for the compound of Example 1, the cataleptic dose is 64-fold higher than the dose which totally inhibits methylphenidate-induced stereotypy.

It is known that the induction of catalepsy is the best factor for evaluation of the side effects of neuroleptics. The results obtained hence permit the conclusion that the compounds of the invention do not induce any side effect of an extrapyramidal nature at the active doses.

EXAMPLE 36

Evaluation of the antipsychotic activity

The protocol used for evaluating the minimum dose which inhibits chewing in rats after the i.p. injection of 40 mg/kg of methylphenidate is identical to that described in Example 35. The results in Table III demonstrate the antipsychotic activity of the compounds of the invention.

TABLE III

| COMPOUNDS | MINIMUM DOSE (mg/kg i.p.) |
|---|---|
| EXAMPLE 20 | 0.31 |
| EXAMPLE 22 | 1.25 |
| EXAMPLE 25 | 0.63 |
| EXAMPLE 26 | 0.31 |
| EXAMPLE 27 | 1.25 |

PHARMACEUTICAL PREPARATION EXAMPLE "

Hard gelatin capsules containing a 2 mg dose of (RS)-3-[1-(benzocyclobuten-1-ylmethyl)-4-piperidyl]-6-fluoro-1,2-benzisoxazole fumarate [D.C.B.P.F.B.]

| D.C.B.P.F.B. | 2 mg |
|---|---|
| Corn starch | 15 mg |
| Lactose | 25 mg |
| Talc | 5 mg |

We claim:

1. A compound selected from the group consisting of: 1,2-benzisoxazole compound of the formula I:

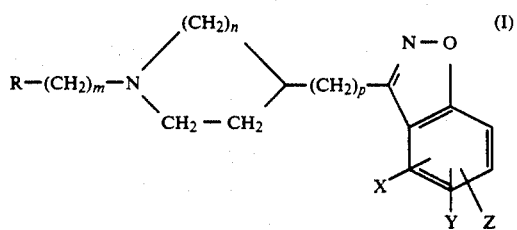

in which m is selected from the group consisting of : zero and the integers 1 to 5, inexlusive, n is 2, p is selected from the group consisting of : 0, 1 and 2, X, Y and Z, which may be identical or different, are each selected from the group consisting of a hydrogen atom, a halogen atom, linear and branched alkyl radicals having 1 to 6 carbon atoms, a trifluoromethyl radical, alkoxy radicals having 1 to 6 carbon atoms, alkylthio radicals having 1 to 6 carbon atoms and a hydroxyl radical, and R is radical of formula C:

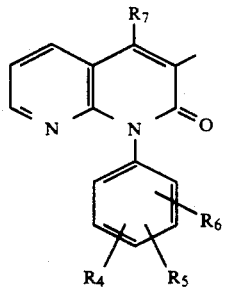

in which $R_4$, $R_5$ and $R_6$, which may be identical or different, are each selected from the group consisting of a hydrogen atom a hydrogen atom, a trifluoromethyl radical, a hydroxyl radical, linear and branched alkyl radicals having 1 to 6 carbon atoms, alkoxy radicals having 1 to 6 carbon atoms and alkylthio radicals having 1to 6 carbon atoms, and $R_7$ is selected from the group consisting of a hydrogen atom and a hydroxyl radical, their optical isomers and their addition salts with a pharmaceutically acceptable organic or inorganic acid.

2. 2-[1-{[1,2-Dihydro-2-oxo-1-(3-trifluoromethylphenyl)-1,8-naphthyridin-3-yl]ethyl}-4-piperidyl]-6-fluoro-1,2-benzisoxazole, a compound of formula I as claimed in claim 1, and its addition salts with a pharmaceutically acceptable inorganic or organic acid.

3. A pharmaceutical composition useful in dopamine and serotonian containing as active antaganism containing as active principle an effective amount of a compound of claim 1, in combination or mixed with a pharmaceutically acceptable, non-toxic, inert vehicle or excipient.

4. A composition of claim 3, wherein the compound is 3-[1-{[1,2-dihydro-2-oxo-1-(3-trifluoromethylphenyl)-1,8-naphthyridin-3-yl]ethyl}-4-piperidyl -6-fluoro-1,2-benzisoxazole.

5. A method for treating a living animal body afflicted with a disease requiring a dopamine and serotonin antagonis comprising the step of administering to the said living animal an amount of a compound of claim 1 which is effective for the alleviation of the said condition.

6. A method of claim 5, wherein the compound is 3-[1-}[1,2-dihydro-2-oxo-1-(3-trifluoromethylphenyl)-1,8-naphthyridin-3-yl]ethyl}-4-piperidyl]-6-fluoro-1,2-benzisoxazole.

* * * * *

UNITED STATES PATENT AND TRADEMARK OFFICE
CERTIFICATE OF CORRECTION

PATENT NO. : 5,134,147

DATED : Jul. 28, 1992

INVENTOR(S) : Jean L. Peglion, Francis Colpaert

It is certified that error appears in the above-identified patent and that said Letters Patent is hereby corrected as shown below:

Column 1, line 6; "1990." should read -- 1990, now U.S. Pat. No. 5,100,902, issued 3-31-92. --.
Column 2, line 62; "hydrogen, atom," should read --hydrogen atom,--. (PA 10-14-91, P. 1, "P. 3, line 21:")
Column 7, approximately line 62, in formula "XIV"; "N" should read -- HN --.
Column 13, line 5; "[2-" should read -- (2- --.
Column 13, approximately line 30; "7.2 7.1" should read --7.2 + 7.1--.
Column 13, line 49; "ppm, 2H" should read --ppm, g, 2H --.
Column 14, approximately line 17; "1-[1-" should read --1-[(1- --.
Column 14, last line; "piperidyl)]" should read --piperidyl]--.
Column 15, line 13; insert a period after "compound".
Column 15, line 18; "ppm, 2H" should read --ppm, m, 2H; --.
Column 16, approximately line 22; "zofuranylmethyl-4-" should read -- zofuranylmethyl)-4- --.
Column 17, approximately line 62; "piperidyl)" should read -- piperidyl] --.
Column 19, line 45; "6.75 ppm, 1H;" should read --6.75 ppm, s, 1H; --.
Column 19, line 50; "4piperidyl]" should read -- 4-piperidyl] --.
Column 21, line 3; "amino-3-" should read -- amino]-3- --.
Column 21, line 41; "dd," should read -- 2d, --.
Column 21, approximately line 47; "-3-yllethanol" should read -- -3-yl]ethanol --.
Column 22, approximately line 53; "benzisoxazole" should read --benzisoxazole fumarate --.
Column 24, line 59; "3.55 ppm, 2H;" should read -- 3.55 ppm, m, 2H;".
Column 24, line 59; "4.2 ppm, 1H;" should read -- 4.2 ppm, m, 1H;".
Column 25, line 11; 5.95 ppm, 2H;" should read -- 5.95 ppm, s, 2H; --.
Column 25, line 24; "3.65 ppm, 1H;" should read -- 3.65 ppm, m, 1H; --.

Page 1 of 5

UNITED STATES PATENT AND TRADEMARK OFFICE
CERTIFICATE OF CORRECTION

PATENT NO. : 5,134,147

DATED : Jul. 28, 1992

INVENTOR(S) : Jean L. Peglion, Francis Colpaert

It is certified that error appears in the above-identified patent and that said Letters Patent is hereby corrected as shown below:

Column 25, approximately line 41; "1H; 4.25 ppm, 2H; 5.95 ppm, 2H;" should read -- 1H; 4.25 ppm, m, 2H; 5.95 ppm, s, 2H; --.
Column 26, line 3; "3-}- 1" should read -- 3- {1 --.
Column 26, line 23; "3-(1-" should read -- 3-{1- --.
Column 26, approximately line 39; "[1.2-" should read --[1,2- --.
Column 26, approximately line 39; "-1.8-" should read -- -1,8- --.
Column 26, approximately line 40; "ethyl)-4-piperidyl-6" should read -- -- ethyl}-4-piperidyl -6 --.
Column 26, approximately line 40; "1.2-" should read -- 1,2- --.
Column 26, approximately line 45; "Flurochenyl" should read -- Fluorophenyl --.
Column 27, line 4; "1piperidyl" should read -- 1-piperidyl --.
Column 27, line 17; "ppm,6H;" should read -- ppm, m, 6H; --.
Column 27, line 18; "ppm, 3H;" should read -- ppm, m, 3H; --.
Column 27, line 42; "piperidyl[-1,2-" should read -- piperidyl]-1,2- --.
Column 28, line 8; insert a period "." after "ethanol".
Column 28, approximately line 46; "2.85 ppm, 1H;" should read -- 2.85 ppm, dd, 1H; --.
Column 28, line 46; "3.5 ppm, 3H; should read --3.5 ppm, m, 3H--.
Column 28, line 46; "3.9 ppm, 1H" should read --3.9 ppm, m, 1H--.
Column 28, line 55; "chloro-35 1-" should read --chloro-1- --.
Column 29, line 3; "-3-{1-" should read -- -3-[-1 --.
Column 29, line 4; "[-1," should read -- ]-1, --.
Column 29, approximately line 9; "[difuran" should read -- ]difuran --.
Column 29, line 67; "4.5 ppm, 2 H;" should read -- 4.5 ppm, t, 2H; --.
Column 30, approximately line 13; "3.7 ppm, 2H;" should read -- 3.7 ppm, m, 2H; --.
Column 30, approximately line 26; "2.85 ppm, 1H;" should read -- 2.85 ppm, m, 1H --.
Column 30, line 27; "ppm, 1H;" should read --ppm, m, 1H --.
Column 30, line 27; "ppm, 2H;" should read -- ppm, t, 2H; --.

UNITED STATES PATENT AND TRADEMARK OFFICE
CERTIFICATE OF CORRECTION

PATENT NO. : 5,134,147

Page 3 of 5

DATED : Jul. 28, 1992

INVENTOR(S) : Jean L. Peglion, Francis Colpaert

It is certified that error appears in the above-identified patent and that said Letters Patent is hereby corrected as shown below:

Column 30, line 27; "4.90 ppm, 1H;" should read -- 4.90 ppm, m, 1H; --.

Column 30, line 28; "7.30 ppm, 2H;" should read -- 7.30 ppm, d, 2H; --.

Column 30, approximately line 33; "4,5-b,: should read --4,5-b'--.

Column 30, line 60; "piperid-1,2-" should read --piperid-4-yl-1,2- --.

Column 31, line 39; "(4.5dimethoxybenzocyclobuten-" should read -- (4,5-dimethoxybenzocyclobuten- --.

Column 31, line 39; insert a closing parenthesis ")" after "ylmethyl".

Column 31, line 40; "-piperidyl)-" should read -- -piperidyl]- --.

Column 32, approximately line 28; insert a period after "benzene".

Column 32, approximately line 48; "3.3 ppm, 4H; should read -- 3.3 ppm, m, 4H; --.

Column 32, approximately line 48; "3.6 ppm, 1H;" should read -- 3.6 ppm, m, 1H; --.

Column 32, approximately line 49; "7.0 ppm, 1H;" should read -- 7.0 ppm, d, 1H; --.

Column 32, approximately line 60; "2.85 ppm, 2H;" should read -- 2.85 ppm, t, 2H; --.

Column 32, approximately line 60; "3.2 ppm, 2H;" should read -- 3.2 ppm, t, 2H; --.

Column 33, line 32; "2.85 ppm, 2H;" should read -- 2.85 ppm, t, 2H;--

Column 33, line 32; "5.65 ppm, 1H" should read -- 5.65 ppm, s, 1H --.

Column 34, line 1; "c+t," should read -- g+t, --.

Column 34, approximately line 7; "-4piperidyl" should read -- -4-piperidyl--.

Column 34, line 20; "3.0 ppm, 1H;" should read -- 3.0 ppm, m, 1H; --.

Column 34, line 21/22; "4.4 ppm, 1H; should read --4.4 ppm, t, 1H; --.

Column 34, line 22/23; "4.65 ppm, 1H;" should read --4.65 ppm, m, 1H; --.

Column 34, line 22; "6.85 ppm, 1H;" should read -- 6.85 ppm, s, 1H; --.

Column 34, line 27; "1 TM (4-" should read -- 1-(4- --.

Column 35, approximately line 17/18; "concentrated" should read -- concentrated. --.

UNITED STATES PATENT AND TRADEMARK OFFICE
CERTIFICATE OF CORRECTION

PATENT NO. : 5,134,147

Page 4 of 5

DATED : Jul. 28, 1992

INVENTOR(S) : Jean L. Peglion, Francis Colpaert

It is certified that error appears in the above-identified patent and that said Letters Patent is hereby corrected as shown below:

```
Column 35, line 39; "1.2 ben-" should read -- 1,2-ben- --
Column 36, line 10; "-3-(1-" should read -- -3-[1- --.
Column 36, line 32; "-piperidyl]-2-" should read -- -piperidyl]-1,2- --.
Column 37, line 6; "5.3 g" should read -- 15.3 g --.
Column 37, line 14; "2.85 ppm,, 2H;" should read --2.85 ppm, m, 2H; --.
Column 38, line 12; "1, 2benzisoxazole." should read --1,2-benzisoxazole. --.
Column 38, line 31; "3.7 ppm, 1H;" should read -- 3.7 ppm, m, 1H; --.
Column 39, line 5; "1.2-" should read -- 1,2- --.
Column 39, approximately line 28; "fluoro TM 1,2-" should read --fluoro-1,2- --
Column 40, approximately line 28; "4.2 ppm, 4H;"
    should read -- 4.2 ppm, s, 4H; --.
Column 40, line 41; "Fluoro-3-1-" should read -- Fluoro-3-[1- --.
Column 40, line 42; "1-ylcarbonyl)" should read -- 1-ylmethyl) --.
Column 49, approximately line 13; "EXAMPLE" should read -- EXAMPLE 37 --.
Column 49, approximately line 26; "1,2-" should read --a 1,2- --.
    (PA 10-4-91, P. 1.) (Cl. 1)
Column 49, approximately line 41; "inexlusive," should read -- inclusive --.
    (PA 10-14-91, P. 1, last line) (Cl. 1)
Column 49, line 53; "R is radical" should read -- R is a radical --. (Cl.1)
Column 50, approximately line 17; "a hydrogen atom a hydrogen atom" should
    read -- a hydrogen atom, a halogen atom, --. (PA 10-14-91, Pg. 2, ln. 11)
Column 50, approximately line 21; "carbon atoms and" should read
    --carbon atoms, and--. (PA 10-14-91, P. 2, ln. 13) (Cl. 1)
Column 50, line 21; "1to" should read --1 to --. (Cl. 1)
Column 50, approximately line 28; "2-" should read -- 3- --.(old Cl. 5)(Cl. 2)
Column 50, approximately line 34; "serotonian containing as active
    antaganism contain-" should read -- serotonin antagonism contain- --
    (Cl. 3, old Cl. 10) PA 10-14-91, P. 2, ln, 15,16)
```

UNITED STATES PATENT AND TRADEMARK OFFICE
CERTIFICATE OF CORRECTION

PATENT NO. : 5,134,147

DATED : Jul. 28, 1992

INVENTOR(S) : Jean L. Peglion, Francis Colpaert

It is certified that error appears in the above-identified patent and that said Letters Patent is hereby corrected as shown below:

Column 50, approximately line 41; "piperidyl-6-" should read
-- piperidyl]-6- --. (PA 10-14-91, P. 2/3, old Cl. 12)

Column 50, approximately line 45; "antagonis" should read
-- antagonist, --. (PA 10-14-91, P. 2, ln. 15/16 (old Cl. 11))

Column 50, approximately line 50; "3-[-}" should read
-- 3-[1-£ --. (old Cl. 13, PA 10-14-91, P. 3)

Signed and Sealed this

Fifteenth Day of March, 1994

BRUCE LEHMAN

Commissioner of Patents and Trademarks